US007986994B2

(12) United States Patent
Stadler et al.

(10) Patent No.: US 7,986,994 B2
(45) Date of Patent: *Jul. 26, 2011

(54) METHOD AND APPARATUS FOR DETECTING CHANGE IN INTRATHORACIC ELECTRICAL IMPEDANCE

(75) Inventors: Robert W. Stadler, Shoreview, MN (US); Li Wang, White Bear Township, MN (US)

(73) Assignee: Medtronic, Inc., Minneapolis, MN (US)

( * ) Notice: Subject to any disclaimer, the term of this patent is extended or adjusted under 35 U.S.C. 154(b) by 522 days.

This patent is subject to a terminal disclaimer.

(21) Appl. No.: 10/727,008

(22) Filed: Dec. 3, 2003

(65) Prior Publication Data

US 2004/0172080 A1   Sep. 2, 2004

Related U.S. Application Data

(60) Provisional application No. 60/430,983, filed on Dec. 4, 2002.

(51) Int. Cl.
*A61N 1/365* (2006.01)

(52) U.S. Cl. ............ 607/17; 607/28; 600/506; 600/507; 600/547; 600/484

(58) Field of Classification Search .................. 607/1, 2, 607/17, 20, 28; 600/547, 484, 506, 507
See application file for complete search history.

(56) References Cited

U.S. PATENT DOCUMENTS

| | | | |
|---|---|---|---|
| 4,373,382 A | 2/1983 | Markowitz | |
| 4,823,797 A | 4/1989 | Heinze et al. | ........... 128/419 PG |
| 5,107,833 A | 4/1992 | Barsness | |
| 5,168,871 A | 12/1992 | Grevious | |
| 5,271,395 A * | 12/1993 | Wahlstrand et al. | ............... 607/9 |
| 5,292,343 A | 3/1994 | Blanchette et al. | |
| 5,314,450 A | 5/1994 | Thompson | |
| 5,324,315 A | 6/1994 | Grevious | |
| 5,354,319 A | 10/1994 | Wyborny et al. | |
| 5,383,909 A | 1/1995 | Keimel | |
| 5,545,186 A | 8/1996 | Olson et al. | |
| 5,755,736 A | 5/1998 | Gillberg et al. | |
| 5,836,975 A | 11/1998 | DeGroot | |
| 5,876,353 A | 3/1999 | Riff | |
| 5,957,861 A * | 9/1999 | Combs et al. | ................. 600/547 |
| 6,045,513 A | 4/2000 | Stone et al. | |
| 6,102,874 A | 8/2000 | Stone et al. | |
| 6,104,949 A | 8/2000 | Crick et al. | |
| 6,154,674 A | 11/2000 | Meier | ............................ 607/23 |

(Continued)

OTHER PUBLICATIONS

Lusignan, S.D., et al., "Compliance and Effectiveness of 1 Year's Home Telemonitoring. The Report of a Pilot Study of Patients With Chronic Heart Failure", *The European Journal of Heart Failure*, 2001; 3:723-730.

(Continued)

*Primary Examiner* — Niketa I Patel
*Assistant Examiner* — Alyssa M Alter
(74) *Attorney, Agent, or Firm* — Michael C. Soldner

(57) ABSTRACT

A method and apparatus for detection of changes in impedance a patient that includes generating measured impedances, generating an adaptive baseline trend of the measured impedances corresponding to a first time period, generating a short term trend of the measured impedances corresponding to a second time period less than the first time period, and generating a metric of impedance change between the adaptive baseline trend and one of a most recent measured impedance and the short term trend of the measured impedances.

5 Claims, 16 Drawing Sheets

U.S. PATENT DOCUMENTS

| | | | |
|---|---|---|---|
| 6,221,011 B1 | 4/2001 | Bardy | |
| 6,263,243 B1 | 7/2001 | Lang | 607/17 |
| 6,277,072 B1 | 8/2001 | Bardy | |
| 6,280,380 B1 | 8/2001 | Bardy | |
| 6,280,409 B1 | 8/2001 | Stone et al. | |
| 6,405,085 B1 | 6/2002 | Graupner et al. | 607/17 |
| 6,449,509 B1* | 9/2002 | Park et al. | 607/20 |
| 6,463,326 B1 | 10/2002 | Hartley et al. | 607/20 |
| 6,595,927 B2* | 7/2003 | Pitts-Crick et al. | 600/529 |
| 6,907,288 B2* | 6/2005 | Daum | 607/17 |
| 2001/0011153 A1 | 8/2001 | Bardy | |
| 2001/0021801 A1 | 9/2001 | Bardy | |
| 2001/0039504 A1 | 11/2001 | Linberg et al. | |
| 2002/0026104 A1 | 2/2002 | Bardy | |
| 2003/0125611 A1 | 7/2003 | Bardy | |
| 2005/0124900 A1* | 6/2005 | Stadler et al. | 600/509 |

OTHER PUBLICATIONS

Baer, C.A., et al., "Electronic Home Monitonng of Congestive Heart Failure Patients: Design and Feasibility", *Congestive Heart Failure*, 1999 5:105-113.

Wuerz & Meador, "Effects of Prehospital Medications on Mortality and Length of Stay in Congestive Heart Failure", *Annals of Emergency Medicine*, 21: Jun. 6, 1992, pp. 669-674.

Berman, et al., "Transthoracic Electrical Impedance as a Guide to Intravascular Overload", *Archives Surgery*, 102 pp. 61-62, Jan. 1971.

\* cited by examiner

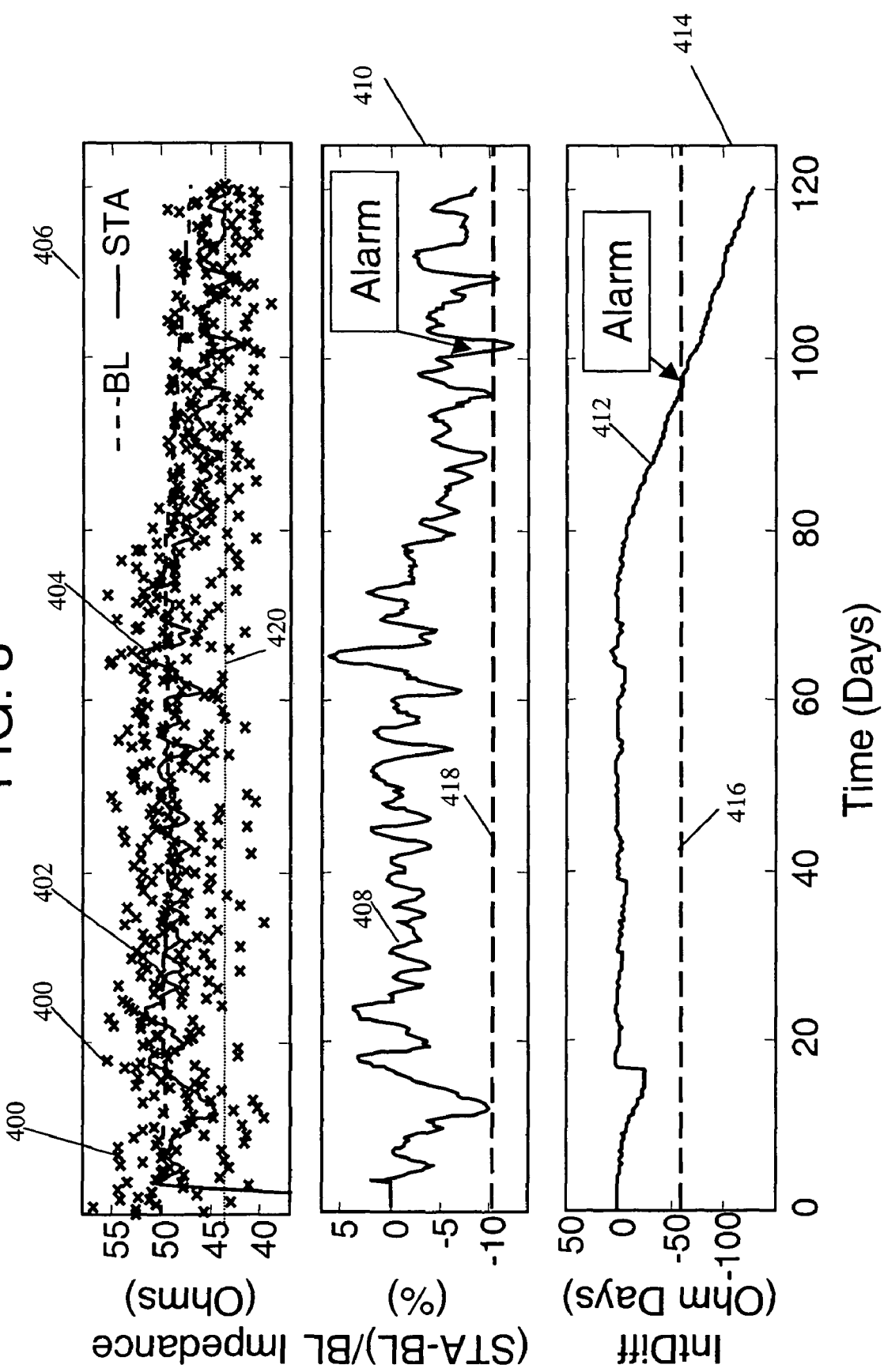

FIG. 11: Step 502 - Fast Adaptation of BL and STA

FIG. 12: Step 514 - Update STA

FIG. 13: Step 516 - Update BL

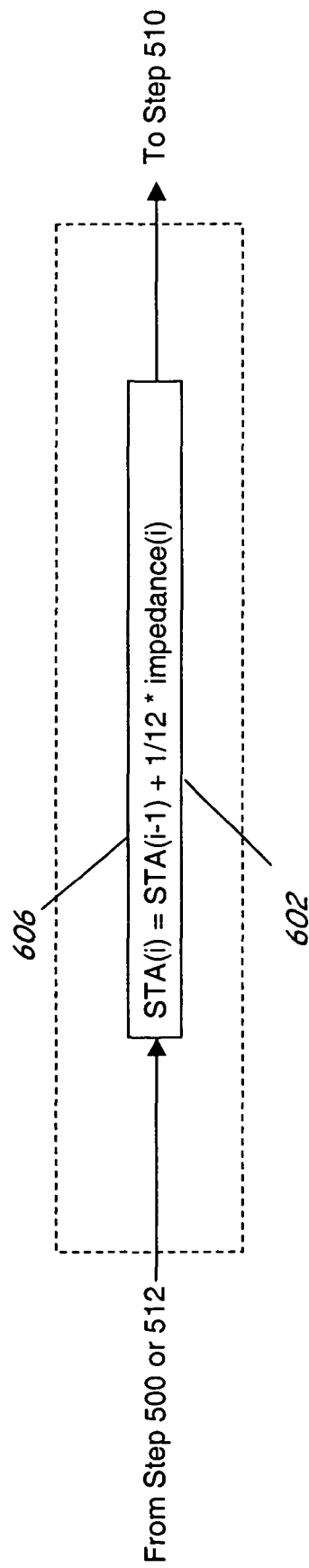
FIG. 15: Step 602 - Fast Adaptation of STA

METHOD AND APPARATUS FOR DETECTING CHANGE IN INTRATHORACIC ELECTRICAL IMPEDANCE

RELATED APPLICATION

The present invention claims priority and other benefits from U.S. Provisional Patent Application Ser. No. 60/430,983, filed Dec. 4, 2002, entitled "METHOD AND APPARATUS FOR DETECTING CHANGES IN INTRATHORACIC ELECTRICAL IMPEDANCE", incorporated herein by reference in its entirety.

FIELD OF THE INVENTION

The present invention generally relates to implantable medical devices, and in particular, the present invention relates to impedance monitoring in an implantable medical device to determine physiological conditions in a patient.

BACKGROUND OF THE INVENTION

Impedance monitoring has been used for determination of numerous physiologic conditions within the body with implanted devices and has been used in external monitoring devices as well. It is commonly understood that transthoracic impedance measurements give a good indication of the fluid status of patients, with decreases in impedance being indicative of increases in fluid content. In an article entitled "Transthoracic Electrical Impedance as a guide to Intravascular Overload" by Berman et. al. (Archives surgery, V102 P61-64 January 1971), electrical impedance methods were used to document the accumulation of fluid in the living tissue. Knowledge of a patient's long-term impedance measurement and changes therein is a valuable clinical indicator of a patient's health, which has heretofore been unavailable to physicians in a very useful form.

While a possible indication of other conditions, the accumulation of fluid can also be an indication of failing heart circulation. There are several mechanisms or diseases that can cause or affect the accumulation of fluid. In general, fluid accumulation is a failure or over response of the homeostatic process within the body. The body normally prevents the build up of fluids by maintaining adequate pressures and concentrations of salt and proteins, and by actively removing excess fluid. Fluid accumulation can occur, for example, when the body's mechanisms for preventing fluid accumulation are affected by disease, such as heart failure, left sided myocardial infarction, high blood pressure, altitude sickness, emphysema (all which affect pressures), cancers that affect the lymphatic system, diseases which disrupt the protein concentrations, and so forth. As a result, providing an adequate monitor of the patient's fluid status can provide physicians and patients with a better tool to manage desease.

It has been demonstrated, for example, in the article "EFFECTS OF PREHOSPITAL MEDICATIONS ON MORTALITY AND LENGTH OF STAY IN CONGESTIVE HEART FAILURE," by Wuerz and Meador, ANNALS OF EMERGENCY MEDICINE, 21:6, June, 1992, pp 669-74, that early pre-hospital treatment for congestive heart failure can save lives. Unfortunately, the first indication that a treating physician would ordinarily have of the occurrence of the accumulation of fluids occurs very late in the disease process with the physical manifestation of swelling or breathing difficulties so overwhelming as to be noticed by the patient who then most often proceeds directly to an emergency room and to hospital admission for fluid overload. On the other hand, with current efforts to reduce the number and length of hospital stays, proactive hospitalization simply to monitor a patient's progression of fluid accumulation is generally not desirable.

Recent attempts at improving more frequent assessment of fluid status without requiring hospital stays are illustrated in the articles "ELECTRONIC HOME MONITORING OF CONGESTIVE HEART FAILURE PATIENTS: DESIGN AND FEASIBILITY", by Baer, C A, DiSalvo T G, Cail M I, Noyes D, and Kvedar J C, Congest Heart Fail. 1999; 5:105-113, and "COMPLIANCE AND EFFECTIVENESS OF 1 YEAR'S HOME TELEMONITORING", by deLusignan S, Wells S, Johnson P, Meredith K, and Leatham E, Eur J Heart Fail. 2001; 3: 723-30, which suggest assessment of fluid status being done daily in the home by the patient, using heart failure scales that measure the patient's weight and instruct the patient to answer a number of questions each day. Although this concept may in fact reduce CHF hospitalizations, daily patient compliance is required and the assessment has to be done in the patient's home, making travel by the patient difficult.

BRIEF DESCRIPTION OF THE DRAWINGS

Other advantages and features of the present invention will be readily appreciated as the same becomes better understood by reference to the following detailed description when considered in connection with the accompanying drawings, in which like reference numerals designate like parts throughout the figures thereof and wherein:

FIG. 8 is a graphical representation of impedance data generated according to an embodiment of the present invention;

FIG. 15 is an exemplary schematic diagram illustrating obtaining initial short term average impedance values, according to an embodiment of the present invention.

DESCRIPTION OF EMBODIMENTS OF THE INVENTION

Figure 1:
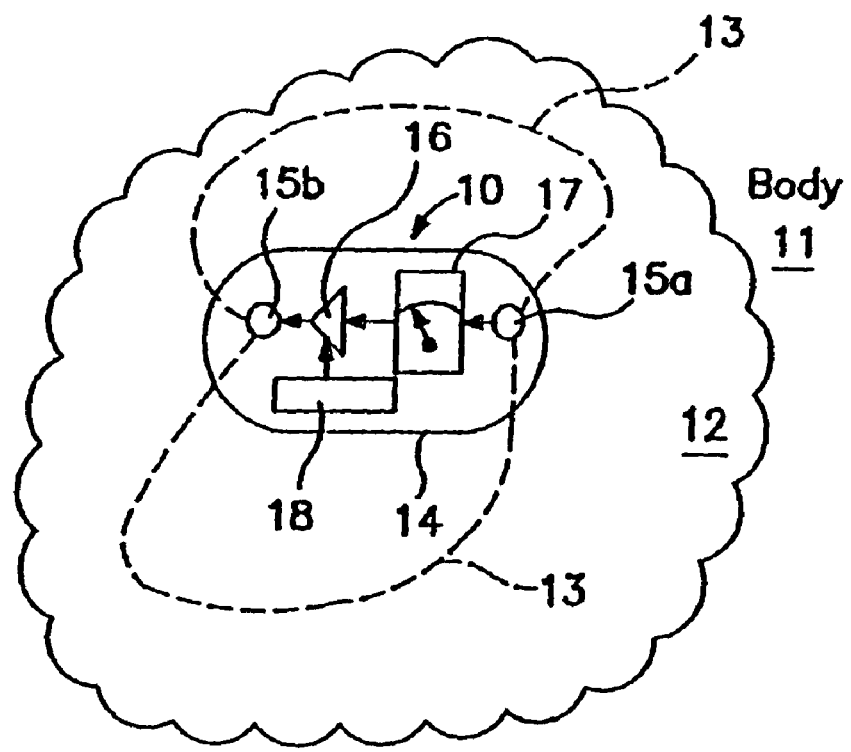
FIG. 1 is a schematic diagram of an implantable medical device according to an embodiment of the present invention.

This invention relates to implantable devices including but not limited to tissue stimulators having measurement capability for determining impedance measurements and is particularly well suited to measure long-term fluid status variations within a living body.

A significant fraction of patients with implanted devices have congestive heart failure and suffer from fluid overload requiring hospitalization. Automated detection of decreases in intrathoracic impedance may lead to advanced warning of fluid overload in patients with congestive heart failure.

A system for determining, generating, monitoring, and using signals representative of fluid status in a living body is described herein. The present invention includes an implantable apparatus for production of impedance measurement in a region of the living body having at least two electrically isolated electrodes, and having within the housing an energy pulse delivery mechanism to deliver electrical pulses to the living body and means for receiving electrical impulses between two or more electrodes so as to determine the impedance of the body between the two or more electrodes.

The energy pulse delivery mechanism may advantageously be provided with an adjustment control that can be used to customize the output for a patient, assist in optimization of the Signal to Noise Ratio (SNR), and avoid local muscle stimulation. Automatic feedback control loops may be used for this purpose, however, in one embodiment of the present invention, both the determination of the preferred pulse delivery electrodes and the values used for the impedance energy pulse to initiate measurement are either factory set or controlled by a telemetry link to the implant during the implant or adjustment procedure.

This invention can be used in conjunction with traditional pacemaker systems and implantable defibrillators, and other implantable devices, or may be incorporated into them. For example, the electrode configuration for impedance measurement may include a cardiac ring electrode or coil electrode positioned in the heart and an electrode on the surface of a pacemaker housing for one measure of impedance. Use of an additional pair of electrodes both located on the housing would enable the use of two different measures of impedance and facilitate the use of comparisons between the resultant signals to refine the signal and provide additional information.

When included within pacemakers, drug pumps or other implantable medical devices, the present invention can be used to alter the delivery of drugs and stimulation pulses to respond to the onset or presence of fluid accumulation or dehydration automatically. In cardiac heart failure (CHF) patients the infusion of diuretics or the application of cardiac resynchronization or cardiac potentiation therapy to manage fluid accumulation are examples of how the present invention could be utilized. It is understood that the term "fluid accumulation" as indicated herein is intended to include both instances of excess fluids accumulating within the patient and instances of in which there are deficiencies in the fluid levels of the patient, indicative of dehydration.

In addition, the present invention may be utilized for providing additional useful data or for reference by an automatic triggering apparatus to store data (in looping or non-looping memories) or generate alarms or take other actions based on significant events, ECG signal reading, pedal impact or other activity sensors, and sensors for measuring temperature, pressure, oxygen saturation, and so forth may advantageously be included. Where such triggers are used the device can be constructed to perform an appropriate device behavior from a range of preconditioned device behaviors.

The present invention relates to a means for establishing and maintaining a patient-specific baseline impedance value. The baseline impedance value is established rapidly upon initialization of the algorithm, and thereafter, the baseline impedance value adapts slowly up and down based upon the currently measured impedance. Importantly, the rate of increase and decrease of the baseline impedance value can be different. An alarm, indicating a derangement of the measured thoracic impedance, is fired when some metric of the measured impedance compared to the baseline impedance exceeds a programmed value. The present invention teaches rapid establishment of the baseline value of the intrathoracic impedance, immediate or delayed reset of the algorithm after a medical intervention, different rates of rise and decline of the baseline value of the thoracic impedance, accumulation of evidence of fluid overload from a metric of the measured impedance compared to the baseline impedance, and multiple alarms for different types of derangements of the measured impedance.

The present invention provides early warning of fluid accumulation or dehydration in the thorax, most often as a result of cardiac decompensation during heart failure, and provides guidance to physicians or nurses to titrate medications like diuretics and beta blockers in heart failure patients. Patients with heart failure live in a delicate balance. Accumulation of fluid can result in frequent and lengthy hospitalizations. Medications can be effective in reducing the accumulation of fluids, but to date there is no accurate, minimally invasive metric of fluid accumulation. An implanted system to obtain measurements of intrathoracic impedance, as a surrogate measurement of fluid accumulation, has been described previously. The present invention is an algorithm for processing these measurements to make a decision to alarm the patient or physician about changes in the intrathoracic impedance.

FIG. 1 is a schematic diagram of an implantable medical device according to an embodiment of the present invention. In the heuristic drawing of FIG. 1, a section of a body 11 is shown with a cut-away area 12 to allow for illustration of an implantable medical device according to an embodiment of the present invention. As illustrated in FIG. 1, an exemplary embodiment of an implantable medical device 10 includes two electrodes 15a and 15b on the surface of a shell 14 of device 10. Power is provided to the circuitry internal to the shell 14 by a power supply 18, which drives a stimulation circuit 16, sending electrons through various pathways in the body (such pathways are heuristically illustrated as being primarily in the area surrounded by dotted line 13) between electrodes 15a and 15b. An impedance measurement device 17 determines the impedance of the circuit pathway 13.

According to an embodiment of the present invention, because of the possible poor signal characteristics that may be found using the same electrodes for generating the impedance test pulse signal and taking the measurement from the same electrodes, impedance measurements are made in a uniform part (or relatively noiseless area) of the field. One way to do this is using one electrode, electrically isolated from the large surface indifferent electrode (like the can or housing of a pacemaker, device 10, or other implant) to deliver the test pulse, and a second electrically isolated electrode to measure the voltage difference in the tissue between the indifferent electrode and this second electrode. Another embodiment would use two completely independent electrodes in the field to measure the impedance, thus having a quadripolar system. In various configurations of this invention additional electrodes can be imagined for flexibility where needed or to use electrodes on leads locatable in specific places within the field created by the test, or excite pulse.

Figure 2:
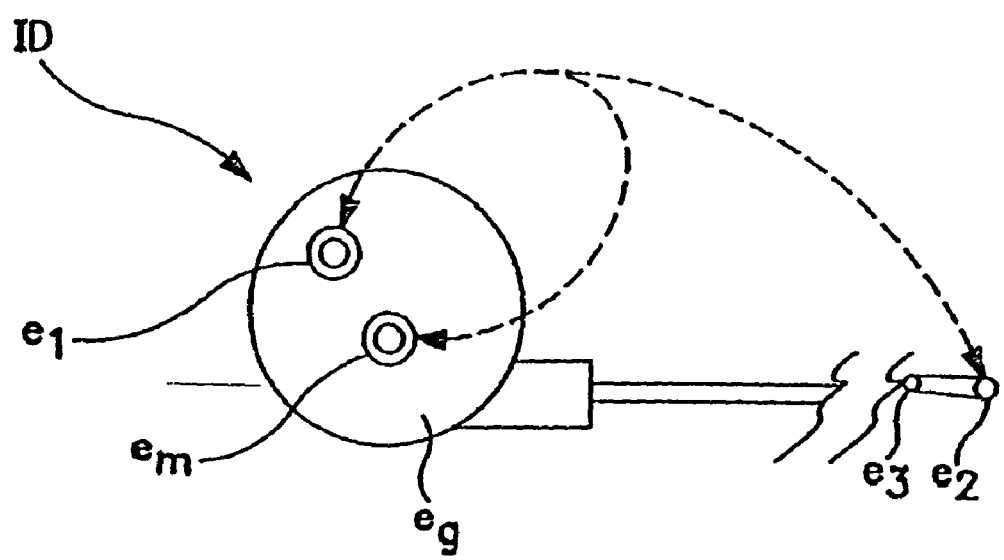
FIG. 2 is a schematic diagram of exemplary electrode configurations in an implantable medical device according to an embodiment of the present invention.

FIG. 2 is a schematic diagram of exemplary electrode configurations in an implantable medical device according to an embodiment of the present invention. This acceptable variety of configuration to achieve different impedance measurement signal values is illustrated, for example, in FIG. 2 wherein an implantable medical device has electrodes e1, e2, eg and em and either electrodes e1 or e2 can be used for developing the test pulses. The value being measured (voltage or impedance of the tissue between these electrode pairs) is taken between another electrically isolated measuring electrode em and the indifferent or ground electrode eg; between em and e1; or between em and e2. Or, of course, the measurement could be taken between the two test pulse delivery electrodes e1, and eg; or between e2 and eg in another embodiment.

As will be described with reference to various figures below, substantial variation can be used for each of the elements described with reference to FIGS. 1-3, and still be within the scope of this invention. For example, according to an embodiment of the present invention, the excitation pulse is delivered between electrodes e3 and eg and the value measured is taken between electrodes e2 and eg. In a exemplary quadrapolar arrangement, the excitation pulse is delivered between electrodes em and e3 and the value measured is taken between electrodes e1 and e2.

Figure 3:
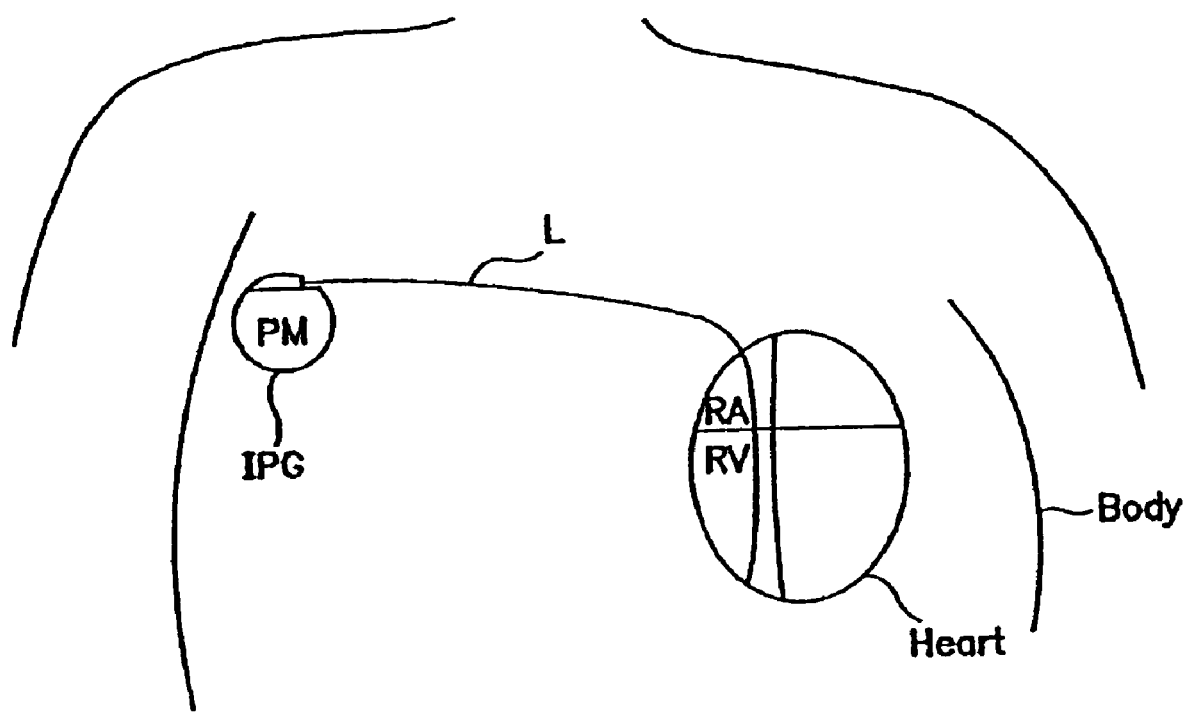
FIG. 3 is a schematic diagram of an exemplary implantable medical device in which the present invention may usefully be practiced.

FIG. 3 is a schematic diagram of an exemplary implantable medical device in which the present invention may usefully be practiced. In FIG. 3 an alternative apparatus for housing the invention is shown in a body having a heart. A pacemaker (IPG) is implanted on the left side or on the right side as shown, and has a lead L extending through the Right Atrium (RA) and into the Right Ventricle (RV) of the heart. By using the circuits and teachings of the present invention, an apparatus such as a pacemaker and lead combination implanted into a living body like that illustrated in FIG. 3 can be used to implement the present invention. Alternative types of implantable medical devices may also be used to house the invention, including for example, defibrillators, drug infusion devices, spinal cord stimulators or any other implantable device having the minimum external number of electrodes and being provided with an impedance stimulation and measurement circuit.

Figure 4:
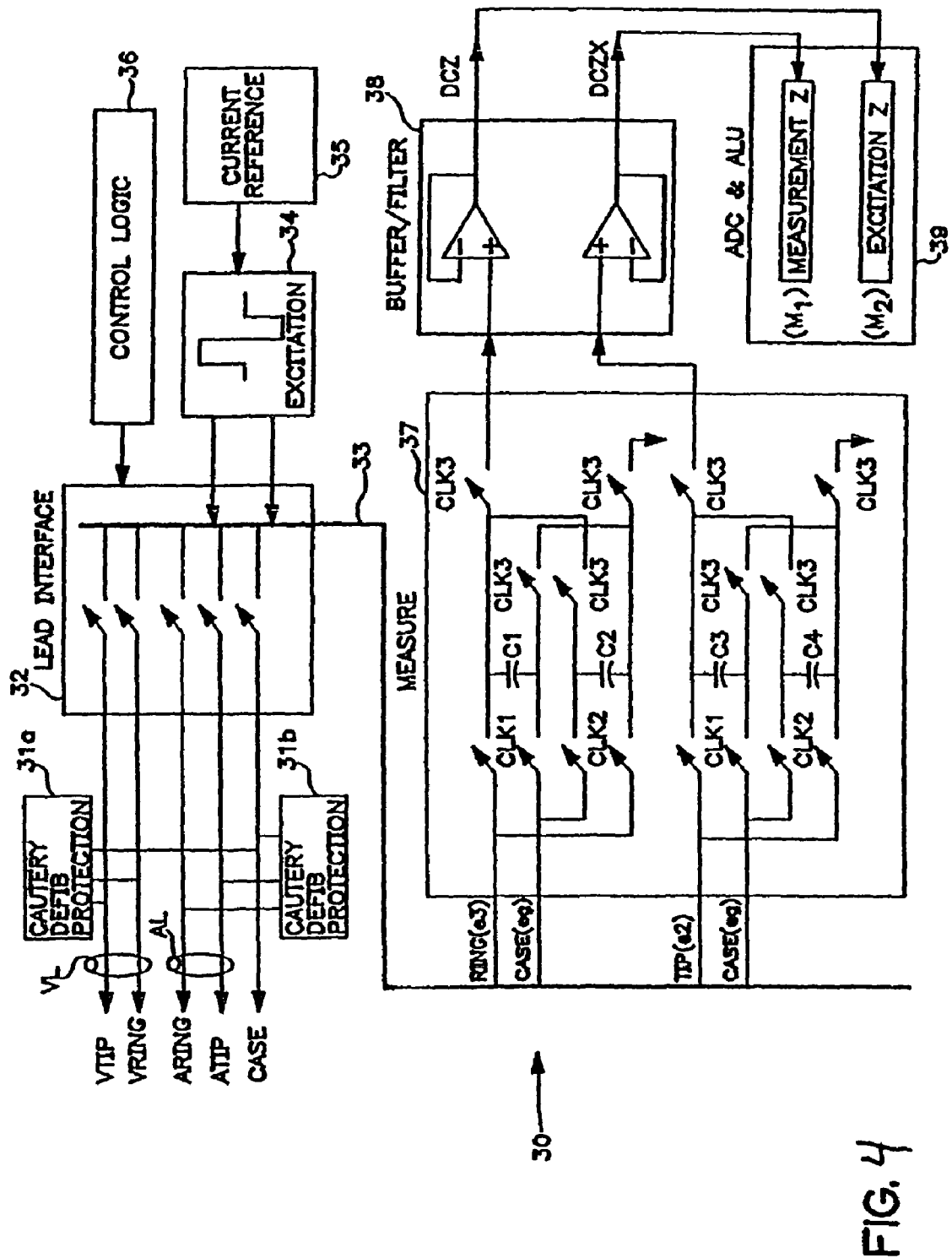
FIG. 4 is a schematic diagram of a monitoring circuit included in an exemplary implantable medical device in which the present invention may usefully be practiced.

FIG. 4 is a schematic diagram of a monitoring circuit included in an exemplary implantable medical device in which the present invention may usefully be practiced. An embodiment of the present invention is described with reference to FIG. 4, in which a block diagram 30 is included which illustrates the addition of an impedance monitoring circuit to a dual chamber two lead pacemaker system. Other sensors may be included in the implantable medical device for additional beneficial data generation purposes, and data therefrom is temporally matched with the impedance data to provide additionally beneficial diagnostic data. Each sensor can be thought of as a system for providing an indication of patient condition, either when it's output is taken alone or combined in manners known to those in the art to determine patient condition. Such included sensor systems or subsystems could include, for example, diurnal cycle indicators, position or posture indicators, resting indicators, heart beat cycle indicators, breathing indicators, movement indicators, and so forth, each providing a signal value that could be stored or used to trigger an activity of the implanted device.

Referring now to FIG. 4, it will be understood by those of ordinary skill in the art that a ventricular lead VL will have a V tip electrode and a V ring electrode and an atrial lead AL will have an A ring electrode and an A tip electrode and that these electrodes are adopted to be inserted within into the ventricle and the atrium of a patient. A case electrode (or neutral electrode as it may be called) is also provided to the circuit so that measurement may be made between any one of the four electrodes and the case, (or between any two electrodes if it is desired not to measure the impedance between an extended lead electrode and the case). In any device having an electrode in the heart and an electrode located substantially away from the heart such as here with the case electrode in the pacemaker pocket, the kind of transthoracic impedance measurement that will be obtained enables the assessment of thoracic fluid status according to the present invention.

Protection circuits are often provided in implanted devices such as circuits 31A and 31B in order to protect the more sensitive electronics of the device from electrosurgical cautery in, or defibrillation of, the patient. A lead interface 32 (usually within the pacemaker shell itself and not in the connector block) provides connection between the electrodes and sources of electrical stimulation as well as circuits for measurement. An excitation circuit 34 (usually associated with a current reference circuit 35) and a control logic circuit 36 also supply input to the lead interface 32. As various switching circuits are well know to those of ordinary skill in the art the use of a large scale line 33 (a control bus) to provide electrical connection to the measurement circuit 37 is shown here to obviate the need to show all possible connections. Measurement circuit 37 captures the resulting voltage from the excitation provided by circuit 34 and functions as a sample and hold circuit between measurements. The input impedance of this block is preferably very large compared to the excitation and measurement path so as not to affect the result. Preferable values for capacitors C1-C4 are substantially within the ranges of 2 pF-50 pF based on the current excitation to allow complete charging in an excitation cycle and realization in a integrated circuit design.

Figure 5:
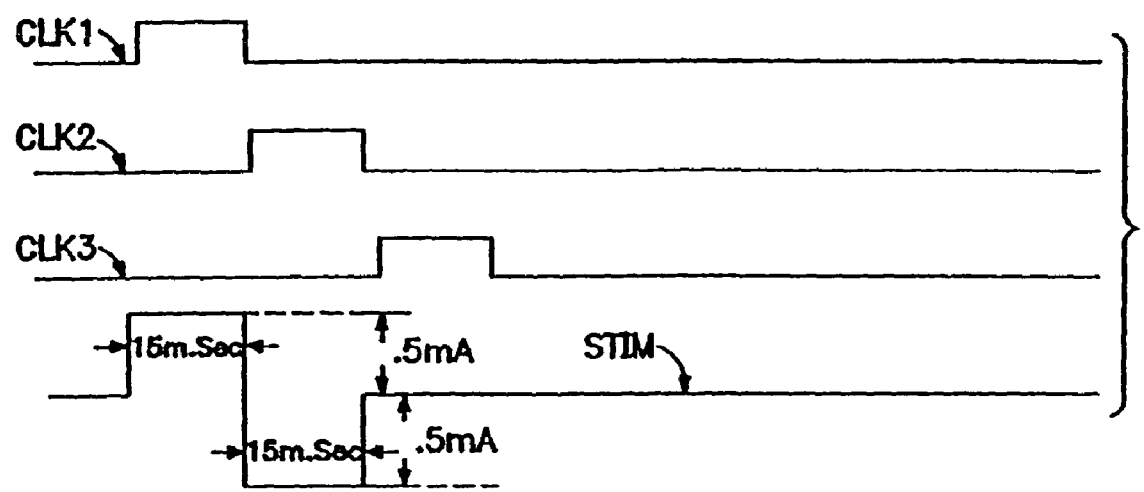
FIG. 5 is a graphical representation of a timing sequence utilized in the monitoring circuit of FIG. 4 according to an embodiment of the present invention.

FIG. 5 is a graphical representation of a timing sequence utilized in the monitoring circuit of FIG. 4 according to an embodiment of the present invention. Measurement circuit 37 is run of course by a clock which in this embodiment has three signals, illustrated in FIG. 4 and in FIG. 5 as CLK 1, CLK 2, and CLK 3 to time the switches. During CLK 1 the top plate of capacitor C1 is connected to the ring and the bottom plate is connected to the case (the reference). The capacitor C3 top plate is connected to the tip electrode and its bottom plate is connected to the case. This arrangement and timing stores the positive peak voltage on capacitors C1 and C3.

During CLK 2 the top plate of capacitor C2 is connected to the case electrode and the bottom plate is connected to the ring. The capacitor C4 top plate is connected to the case electrode and the bottom plate is connected to the tip electrode. This results in the peak voltage during the negative phase of the excitation being stored on capacitors C2 and C4.

The clock signal phase CLK 3 connects the top plate of capacitors C1 to the top plate of capacitor of C2 with the reference connected to the ground. The top plate of capacitor C3 is also connected to the top plate of capacitor C4. This results in the peak-to-peak excitation voltage on capacitors C1 plus C2 and peak-to-peak measurement voltage on capacitors C3 and C4.

Numerous alternative circuit arrangements are within the skill of the ordinary artisan and could be employed as an alternative to the circuit described here, but it is believed that it will be advantageous to design the circuit with certain constraints. Particularly relevant is having the test pulse delivery occur synchronously to the timing of the impedance measurement. Also depending on the location of the electrodes used for measurement, it is advantageous to consider synchronization to the heart beat cycle and the respiratory cycles or the variation in measurement resulting from measuring at inconsistent times within these cycles may cause insurmountable difficulties in extracting useful signal from the impedance changes created by these cycles.

In FIG. 5, the timing diagram for switching the CLK switches (CLK 1-3) and their timing in relation to the stimulation signal STIM, are shown. It should be recognized that the current (I) ranges from about 1 mA peak-to-peak 10 uA peak-to-peak peak and can be selected depending on the device used for the impedance measurement and other factors which would be apparent to one of ordinary skill in the art. The convenient current reference block 35 of FIG. 4 could be used for this adjustment.

Figure 6:
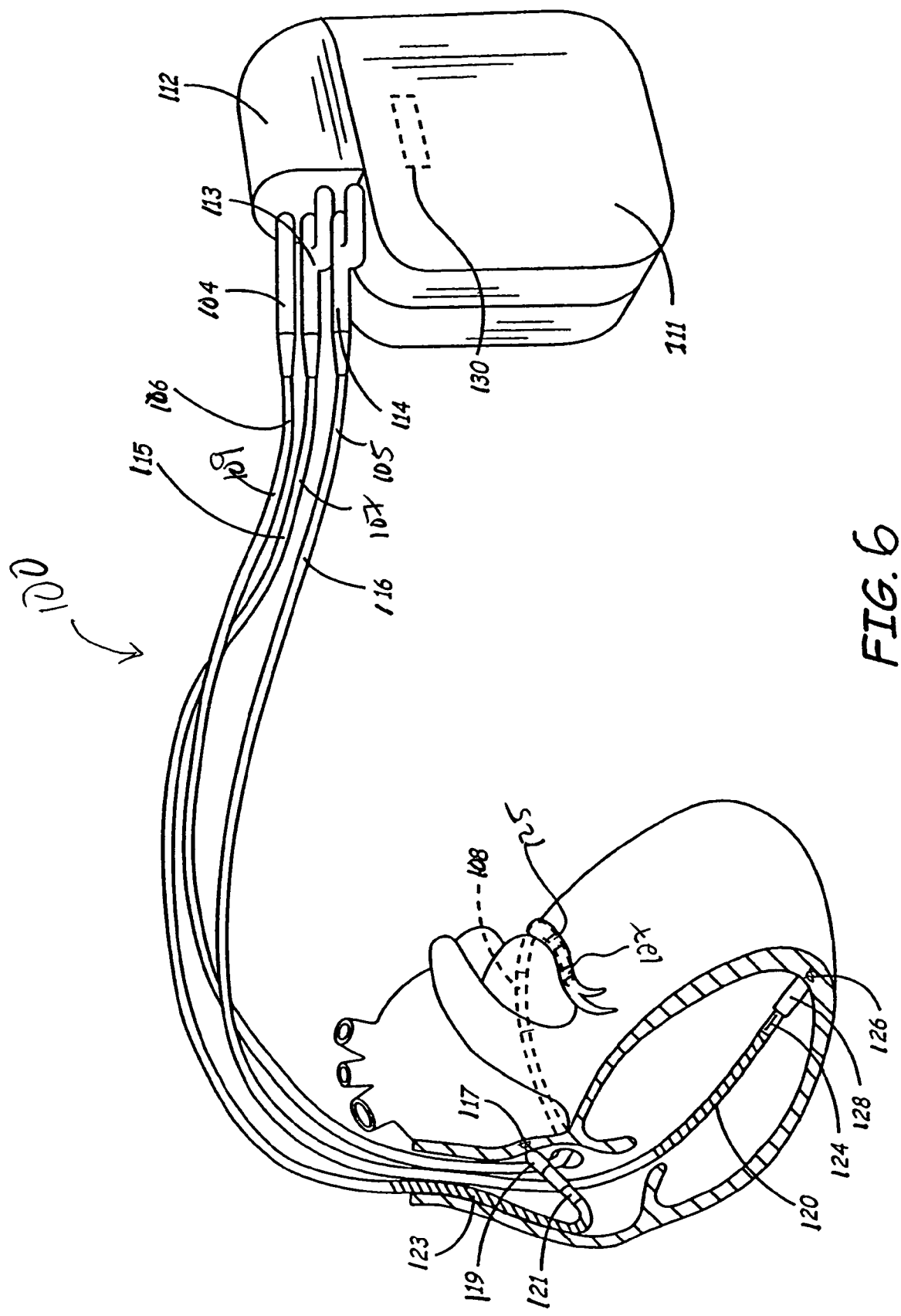
FIG. 6 is a schematic diagram of an implantable medical device in which the present invention may usefully be practiced according to an embodiment of the present invention.

FIG. 6 is a schematic diagram of an implantable medical device in which the present invention may usefully be practiced according to an embodiment of the present invention. As illustrated in FIG. 6, an implantable medical device 100 according to an embodiment of the present invention includes a ventricular lead 105 having an elongated insulative lead body 116 carrying three mutually insulated conductors. Located adjacent the distal end of the lead 105 are a ring electrode 124, an extendable helix electrode 126, mounted retractably within an insulative electrode head 128, and an elongated coil electrode 120. Each of the electrodes 120, 124 and 126 is coupled to one of the three conductors within the lead body 116. Electrodes 124 and 126 are employed for cardiac pacing and for sensing ventricular depolarizations, and electrode 120 is employed for cardioversion and/or defibrillation and for sensing depolarizations, as described below. At the proximal end of the lead 105 is a bifurcated connector 114, which carries three electrical connectors, each coupled to one of the coiled conductors.

An atrial/SVC lead 107 includes an elongated insulative lead body 115, also carrying three mutually insulated conductors. Located adjacent the J-shaped distal end of the lead 107 are a ring electrode 121 and an extendible helix electrode 117, mounted retractably within an insulative electrode head 119. Each of the electrodes 117 and 121 is coupled to one of the conductors within the lead body 115. Electrodes 117 and 121 are employed for atrial pacing and for sensing atrial depolarizations. An elongated coil electrode 123 is provided, proximal to electrode 121 and coupled to the third conductor within the lead body 115. At the proximal end of the lead 107 is a bifurcated connector 113, which carries three electrical connectors, each coupled to one of the coiled conductors.

Any other known lead configurations may also be utilized other the lead configuration of FIG. 6. For example, coil electrode 123 could be located on ventricular lead 105 and positioned within the atrium or SVC by ventricular lead 105 rather than by atrial lead 107.

A coronary sinus/coronary vein lead 109 includes an elongated insulative lead body 106, carrying three conductors, one of which is coupled to an elongated coiled defibrillation electrode 108. Electrode 108, illustrated in broken outline, is located within the coronary sinus and great vein of the heart. Located adjacent the distal end of lead 109 are a ring electrode 125 and a tip electrode 127. Each of electrodes 125-127 is coupled to one of the remaining two of the three conductors located within lead body 106. At the proximal end of the lead 109 is a connector plug 104 that carries an electrical connector, coupled to the coiled conductors.

The implantable medical device 100 includes a hermetically sealed enclosure 111 containing the electronic circuitry (FIG. 7) used for generating cardiac pacing pulses for delivering cardioversion and defibrillation shocks and for monitoring the patient's heart rhythm. Implantable medical device 110 is shown with the lead connector assemblies 104, 113 and 114 inserted into the connector block 112, which serves as a receptacle and electrical connector for receiving the connectors 104, 113 and 114 and interconnecting the leads to the circuitry within enclosure 111.

Insulation of the outward facing portion of the housing 111 of the implantable medical device 110 may be provided or a portion 130 of the outward facing portion may instead be left uninsulated, or some other division between insulated and uninsulated portions may be employed. The uninsulated portion 130 of the housing 111 optionally serves as a subcutaneous defibrillation electrode, used to defibrillate either the atria or ventricles, and as a sensing electrode for sensing depolarizations of the heart. Other lead configurations and electrode locations may of course be substituted for the lead set illustrated. For example, atrial defibrillation and sensing electrodes might be added to either the coronary sinus lead or the right ventricular lead instead of being located on a separate atrial lead, allowing for a two lead system.

Figure 7:
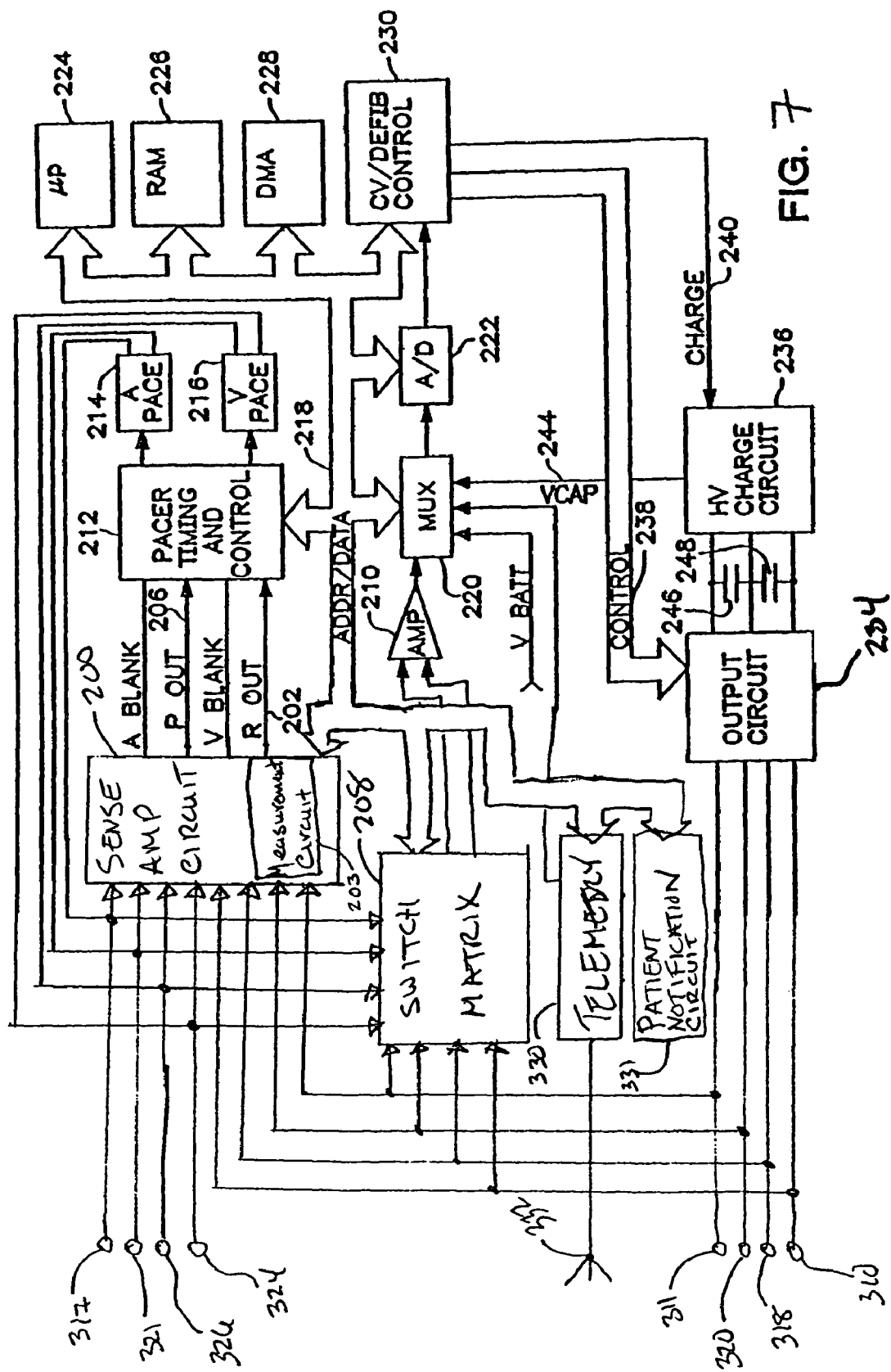
FIG. 7 is a functional block diagram of an exemplary implantable medical device of the type illustrated in FIG. 6, in which the present invention may usefully be practiced.

FIG. 7 is a functional block diagram of an exemplary implantable medical device of the type illustrated in FIG. 6, in which the present invention may usefully be practiced. The device is provided with a lead system including electrodes, which may be as illustrated in FIG. 6. Alternate lead systems may of course be substituted. If the electrode configuration of FIG. 6 is employed, the correspondence to the illustrated electrodes is as follows. Electrode 311 corresponds to an electrode formed along the uninsulated portion 130 of the housing of the implantable medical device 110. Electrode 320 corresponds to electrode 120 and is a defibrillation electrode located in the right ventricle. Electrode 310 corresponds to electrode 108 and is a defibrillation electrode located in the coronary sinus. Electrode 318 corresponds to electrode 123 and is a defibrillation electrode located in the superior vena cava. Electrodes 324 and 326 correspond to electrodes 124 and 126, and are used for sensing and pacing in the ventricle. Electrodes 317 and 321 correspond to electrodes 117 and 121 and are used for pacing and sensing in the atrium.

Electrodes 310, 311, 318 and 320 are coupled to high voltage output circuit 234. Electrodes 324 and 326 are coupled to an R-wave amplifier, which preferably takes the form of an automatic gain controlled amplifier providing an adjustable sensing threshold as a function of the measured R-wave amplitude, included in a sense amplifier circuit 200. A signal is generated on R-out line 202 whenever the signal sensed between electrodes 324 and 326 exceeds the present sensing threshold.

Electrodes 317 and 321 are coupled to a P-wave amplifier, which preferably also takes the form of an automatic gain controlled amplifier providing an adjustable sensing threshold as a function of the measured P-wave amplitude, included in sense amplifier circuit 200. A signal is generated on P-out line 206 whenever the signal sensed between electrodes 317 and 321 exceeds the present sensing threshold. The general operation of the R-wave and P-wave amplifiers of sense amplifier circuit 200 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety. However, any of the numerous prior art sense amplifiers employed in implantable cardiac pacemakers, defibrillators and monitors may also usefully be employed in conjunction with the present invention.

Switch matrix 208 is used to select which of the available electrodes are coupled to wide band amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

Telemetry circuit 330 receives downlink telemetry from and sends uplink telemetry to the patient activator by means of antenna 332. Data to be uplinked to the activator and control signals for the telemetry circuit are provided by microprocessor 224 via address/data bus 218. Received telemetry is provided to microprocessor 224 via multiplexer 220. The atrial and ventricular sense amp circuits of sense amplifier circuit 200 produce atrial and ventricular EGM signals which also may be digitized and uplink telemetered to an associated programmer on receipt of a suitable interrogation command. The device may also be capable of generating so-called marker codes indicative of different cardiac events that it detects. A pacemaker with marker-channel capability is described, for example, in U.S. Pat. No. 4,374,382 to Markowitz, incorporated by reference herein in its entirety. The particular telemetry system employed is not critical to practicing the invention, and any of the numerous types of telemetry systems known for use in implantable devices may be used. In particular, the telemetry systems as disclosed in U.S. Pat. No. 5,292,343 issued to Blanchette et al., U.S. Pat. No. 5,314,450, issued to Thompson, U.S. Pat. No. 5,354,319, issued to Wyborny et al. U.S. Pat. No. 5,383,909, issued to Keimel, U.S. Pat. No. 5,168,871, issued to Grevious, U.S. Pat. No. 5,107,833 issued to Barsness or U.S. Pat. No. 5,324,315, issued to Grevious, all incorporated herein by reference in their entireties, are suitable for use in conjunction with the present invention. However, the telemetry systems disclosed in the various other patents cited herein which are directed to programmable implanted devices, or similar systems may also be substituted. The telemetry circuit 330 is of course also employed for communication to and from an external programmer, as is conventional in implantable anti-arrhythmia devices.

A patient notification circuit 331 enables the patient to be notified in the event that it is determined that a significant change in impedance has occurred, as will be in detail described below.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI, DDDR, VVIR, DVIR, VDDR, AAIR, DDIR and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, PR intervals and R-P intervals, which measurements are stored in memory 226 and are used in conjunction with tachyarrhythmia detection functions.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. Microprocessor 224 includes associated ROM in which the stored program controlling its operation as described below resides. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

Arrhythmia detection may include any of the numerous available prior art tachyarrhythmia detection algorithms. One preferred embodiment may employ all or a subset of the rule-based detection methods described in U.S. Pat. No. 5,545,186 issued to Olson et al. or in U.S. Pat. No. 5,755,736 issued to Gillberg et al., both incorporated herein by reference in their entireties. However, any of the various arrhythmia detection methodologies known to the art might also usefully be employed in alternative embodiments of the invention.

In the event that an atrial or ventricular tachyarrhythmia is detected, and an anti-tachyarrhythmia pacing regimen is desired, timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization. In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse.

A measurement circuit 203, similar to measurement circuit 37 and excitation circuit 34 described above in reference to FIG. 4, is utilized in the delivery of excitation pulses and to measure the resulting impedances between a vector formed by any pair of electrodes selected from among electrodes 310, 311, 317, 318, 320, 321, 324 and 326 through connections made in switch matrix 208. Measurement circuit 203, which is coupled to data/address bus 218, can be separate from or may be included within sense amplification circuit 200, as shown.

According to the present invention, once impedance measurement is initiated by microprocessor 224, an excitation pulse is generated by output circuit 234 and applied across an excitation path corresponding to a vector formed by selected electrodes, described above. The excitation pulse may be in the form of either a current pulse or a voltage pulse, and, in either case, may consist of one or more phases of differing polarity, or may correspond to a monophasic, constant voltage pulse for simplicity of implementation. In an embodiment of the present invention, for example, the excitation pulse has an amplitude of approximately 1 volt and a pulse width of approximately 90 microseconds, although any desired amplitude and pulse width may be utilized.

Measurement circuit 203 measures the voltage appearing across a measurement path corresponding to selected measurement electrodes, with the timing of the measurement by measurement circuit 203 being time by timing and control circuit 212 so as to be synchronized with delivery of the excitation pulse. Using the current delivered across the excitation path and the voltage measured across the measure path, microprocessor 224 then calculates the apparent intra-thoracic impedance using Ohm's Law. The process is repeated, so that multiple excitation pulses are delivered over a multiple number of days to generate multiple impedance measurements.

Figure 7A:
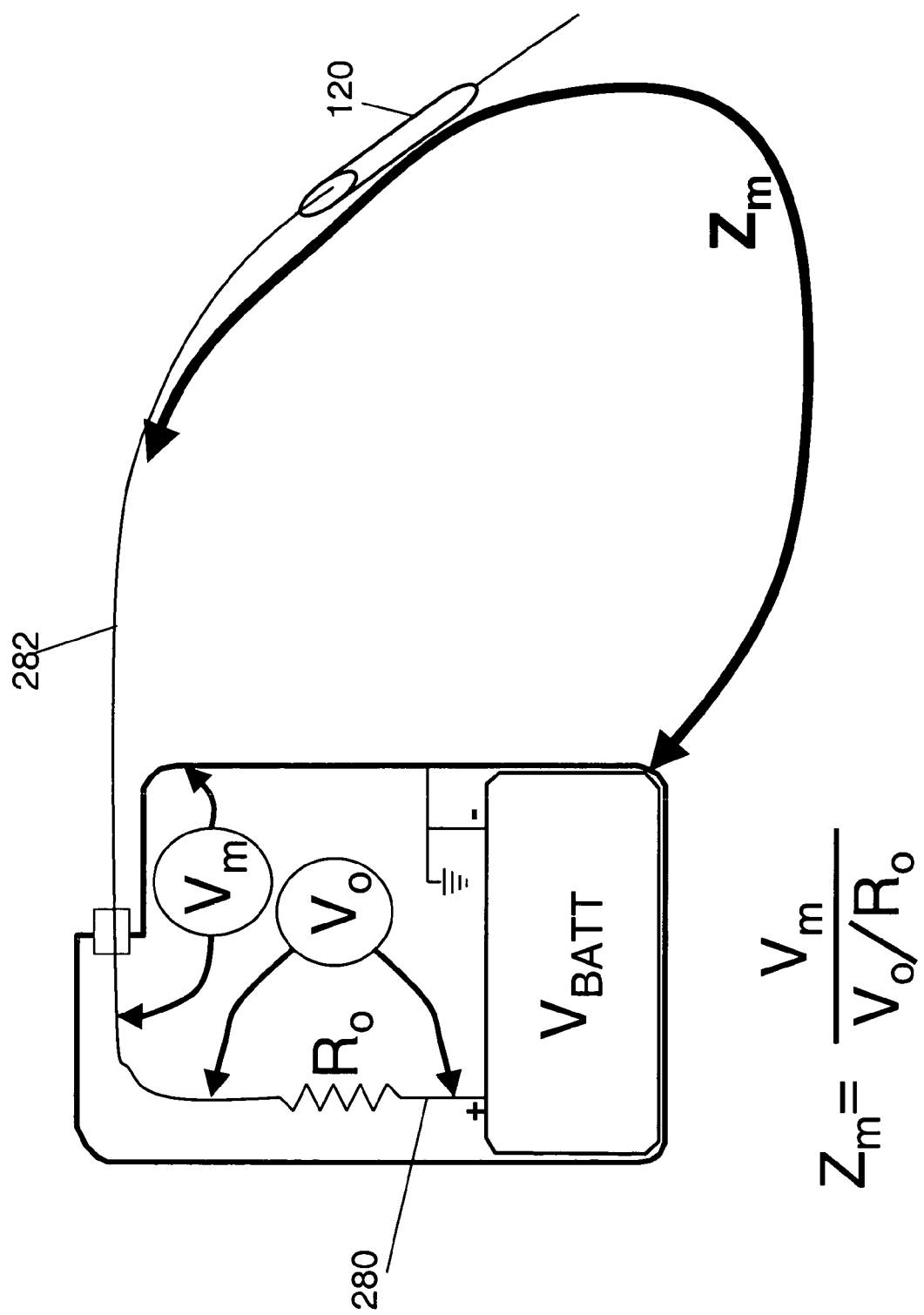
FIG. 7A is a schematic diagram of a method of measuring impedance according to an embodiment of the present invention.

FIG. 7A is a schematic diagram of a method of measuring impedance according to an embodiment of the present invention. For example, according to an embodiment of the present invention, in order to generate a transthoracic impedance $Z_M$ measurement, pacer timing and control circuit 212 initiates, via control circuitry 230, delivery of a predetermined voltage pulse $V_o$ from output circuit 234 along excitation path 280 between electrodes 120 and 130. A resistor $R_O$ incorporated in output circuit 234 is positioned along excitation path 280 having a known resistance so that the current $I_O$ delivered along the excitation path 280 can be calculated, using Ohm's Law, as $I_O = V_O/R_O$. The voltage $V_M$ is measured across the measurement path 282 between a point after resistor $R_O$ and electrode 130, and, knowing the current $I_O$ delivered to the measurement path 282, impedance $Z_M$ is calculated as $Z_M = V_M/(V_O/R_O)$.

According to the present invention, using the resulting impedance measurements, the average of all impedance measurements acquired over a predetermined time period is calculated to obtain a period average impedance. Values of an expected impedance and a short term average (STA) impedance are computed from the period average impedance, and changes in the period average impedance values over time are monitored for indications of fluid accumulation, as will be described below. The expected impedance is an underlying baseline (BL) impedance that is a very low pass filtered version of the period average impedance, and is intended to represent the patient's "dry" impedance when no excessive fluid is present. The value of an expected or baseline impedance varies from patient to patient, and is generally between approximately 50 ohms and 90 ohms. The short term average (STA) impedance is a slightly filtered version of the period average impedance, and is intended to be a best estimate of the current impedance.

FIG. 8 is a graphical representation of impedance data generated according to an embodiment of the present invention. FIG. 9 is a flow chart illustrating a method for determining changes in impedance according to an embodiment of the present invention. Because of post-implant drop and recovery in the impedance measurements that typically occurs immediately after the device is implanted within the patient, the method for determining changes in impedance according to the present invention is not initiated until after a predetermined period of time subsequent to implantation of the device 100 within the patient has expired. An exemplary period post implant may be 30 days, for example, in order to allow for post-operative stabilization of the impedance measurements before the algorithm is activated. Once the initial stabilization time period has expired, the algorithm establishes initial values of the expected, or baseline (BL) impedance, and the short term average (STA) impedance, and begins to search for changes in the impedance measurements obtained from pre-programmed vectors chosen for the excitation path and the measurement path, such as the ring (e3)-case (e2) and tip (e2)-case (eg) arrangement of FIG. 4, or the RV coil electrode 120 and housing electrode 130 being utilized for both the excitation path and the measurement path of FIG. 6, described above, for example. However, it is understood that other arrangements can also be utilized, such as an arrangement in which the excitation path is between electrode 123 and electrode 130 and the measurement path is between electrode 117 and electrode 130.

As illustrated in FIG. 8, a graphical representation of a calculated period average impedance 400 corresponding to the average of individual raw impedance measurements collected a predetermined number of times per day during a predetermined period of the day, as well as calculated values of a baseline impedance 402 and a short term average (STA) impedance 404, shown by a hashed line and a solid line, respectively, are generated in plot 406 from the measured impedances, as described below. In addition, a graphical representation of the difference between the calculated short term average impedance and the calculated baseline impedance as a percentage of the baseline impedance 408 is generated in plot 410, and a graphical representation of the integral of the difference (IntDiff) 412 illustrated by the difference between the baseline impedance 402 and the calculated period average impedance 400 is generated in plot 414. The integral of the difference (IntDiff) 412 accumulates the difference between baseline impedance 402 and the calculated period average impedances 400, as will be described below.

Figure 8A:
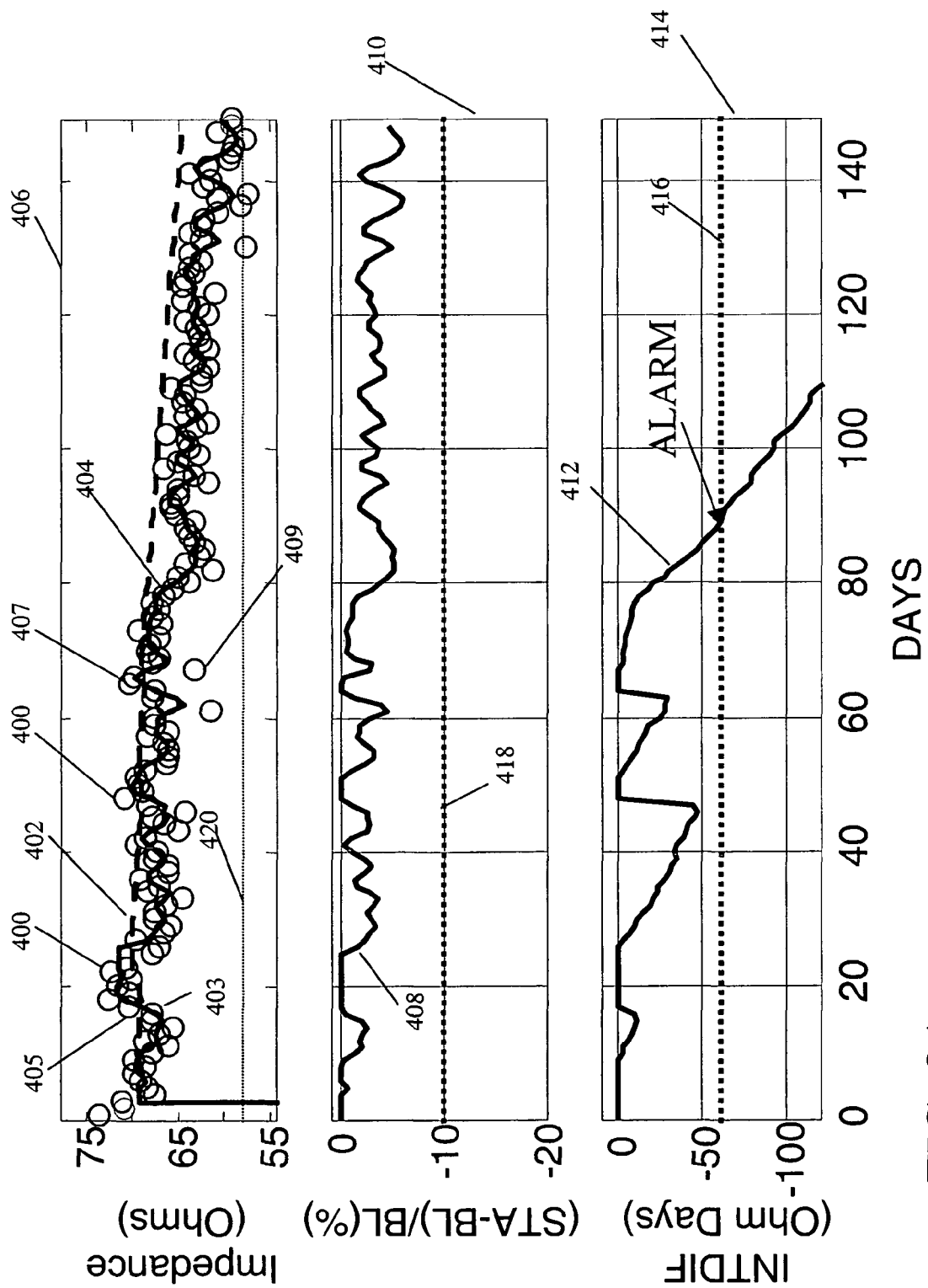
FIG. 8A is an exemplary graphical representation of impedance data generated according to an embodiment of the present invention.
Figure 9:
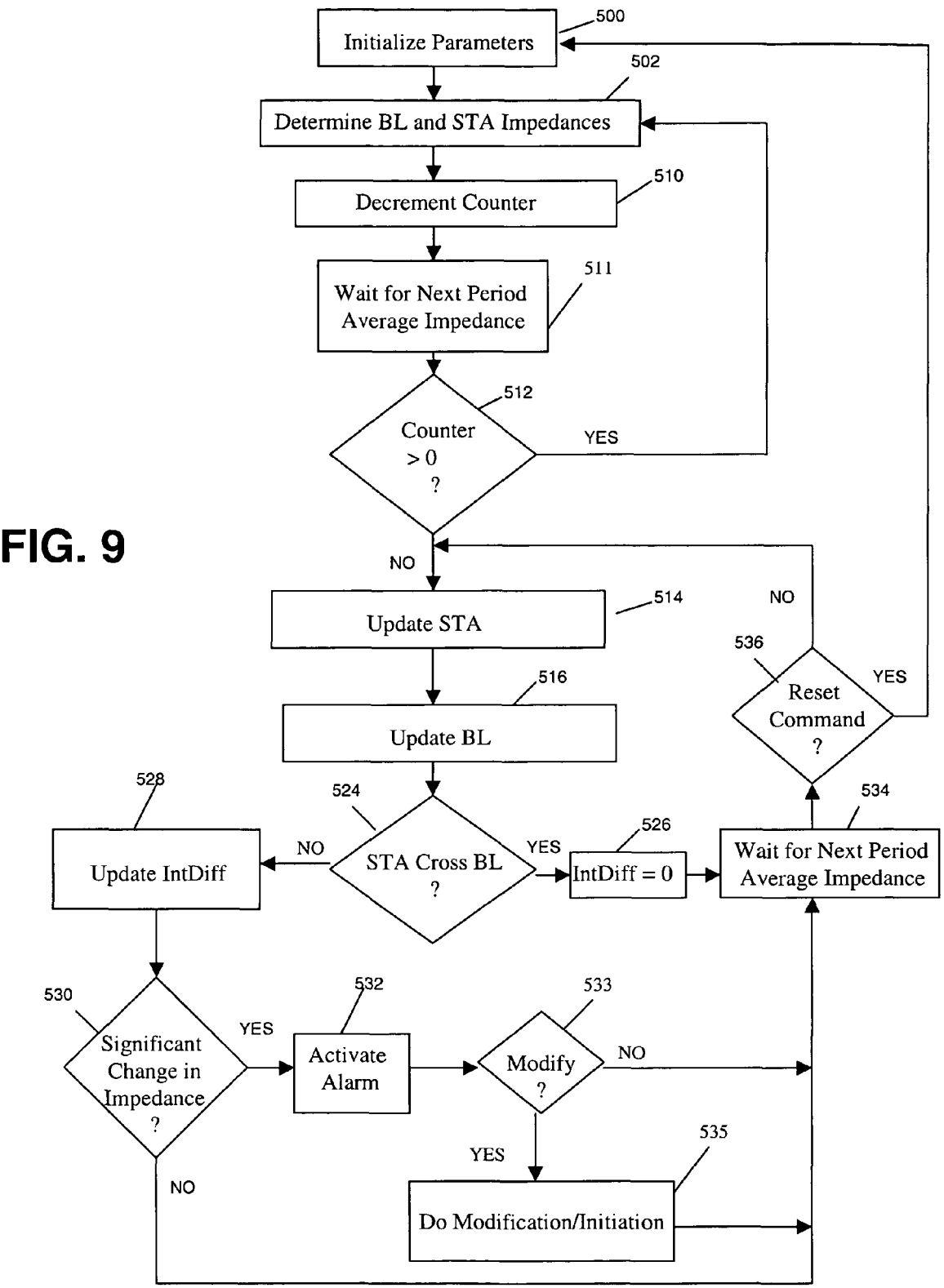
FIG. 9 is a flow chart illustrating a method for determining changes in impedance according to an embodiment of the present invention.

In the example illustrated in FIG. 8, the calculated period average impedance 400 was determined from individual raw impedance measurements that were collected four times per day, such as between the hours of 12-6 am, 6 am-12 pm, 12 pm-6 pm, and 6 pm-12 am, for example, resulting in four calculated period average impedances 400 per day, although it is understood that the present invention is not intended to be limited to this rate, and therefore the present invention would include other possible acquisition rates. FIG. 8A is an exemplary graphical representation of impedance data generated according to an embodiment of the present invention, in which the calculated period average impedance 400 was determined from individual raw impedance measurements that were collected once per day, such as between the hours of 12 pm-5 pm.

According to an embodiment of the present invention, the period average impedance 400 is determined by calculating the average of impedance measurements taken over a predetermined period of time during each day. For example, according to an embodiment of the present invention in which the period average impedance 400 is generated one time per day, graphically represented in FIG. 8A, an period average impedance is determined using 512 impedance measurements taken over a 5 hour period between 12 pm and 5 pm, although any number of impedances may be taken over any desired time period without departing from the invention. In particular, in order to determine a period average impedance, each one hour period between 12 pm and 5 pm is divided into three twenty minute time periods, during which thirty-two impedance measurements are taken, resulting in 15 measurements of 32 impedances. In addition, thirty-two impedance measurements are similarly taken at 5 pm, so that in all 16 measurements of 32 impedances are performed during the period between 12 pm and 5 pm, resulting in a total of 512 impedance measurements (32×16=512) being taken over the 5 hour period each day. A period average impedance value is then determined by calculating an average of the 512 impedances generated during the predetermined time period, i.e., between 12 pm and 5 pm.

A similar process would be utilized in an embodiment in which the period average impedance 400 is generated four times per day, graphically represented in FIG. 8, based on a predetermined number of impedances collected over each of the four time periods, i.e., between the hours of 12 am-6 am, 6 am-12 pm, 12 pm-6 pm, and 6 pm-12 am. For example, in an embodiment of the present invention, each hour of the four six hour periods are divide three 20 minute periods so that in all 20 measurements of 32 impedances are performed in each of the 4 time periods resulting in a total of 640 impedance measurements (32×20+640) in each of the four 6 hour time periods, resulting in the need for 2,560 raw impedance values a day.

In any case, the goal of the design of the impedance sampling scheme for calculation of the period average impedance is to exclude the contributions of undesirable impedance modifying factors, including all impedance changes that are unrelated to the patient's underlying fluid status, such as cardiac cycle, respiratory cycle, activity level, posture, etc. It is noteworthy that the undesirable impedance modifying factors operate on shorter time scales than true changes in the patient's fluid status, and therefore appropriate sampling and averaging schemes such as those examples presented above can be used to exclude the contributions of these undesirable impedance modifying factors.

Figure 10:
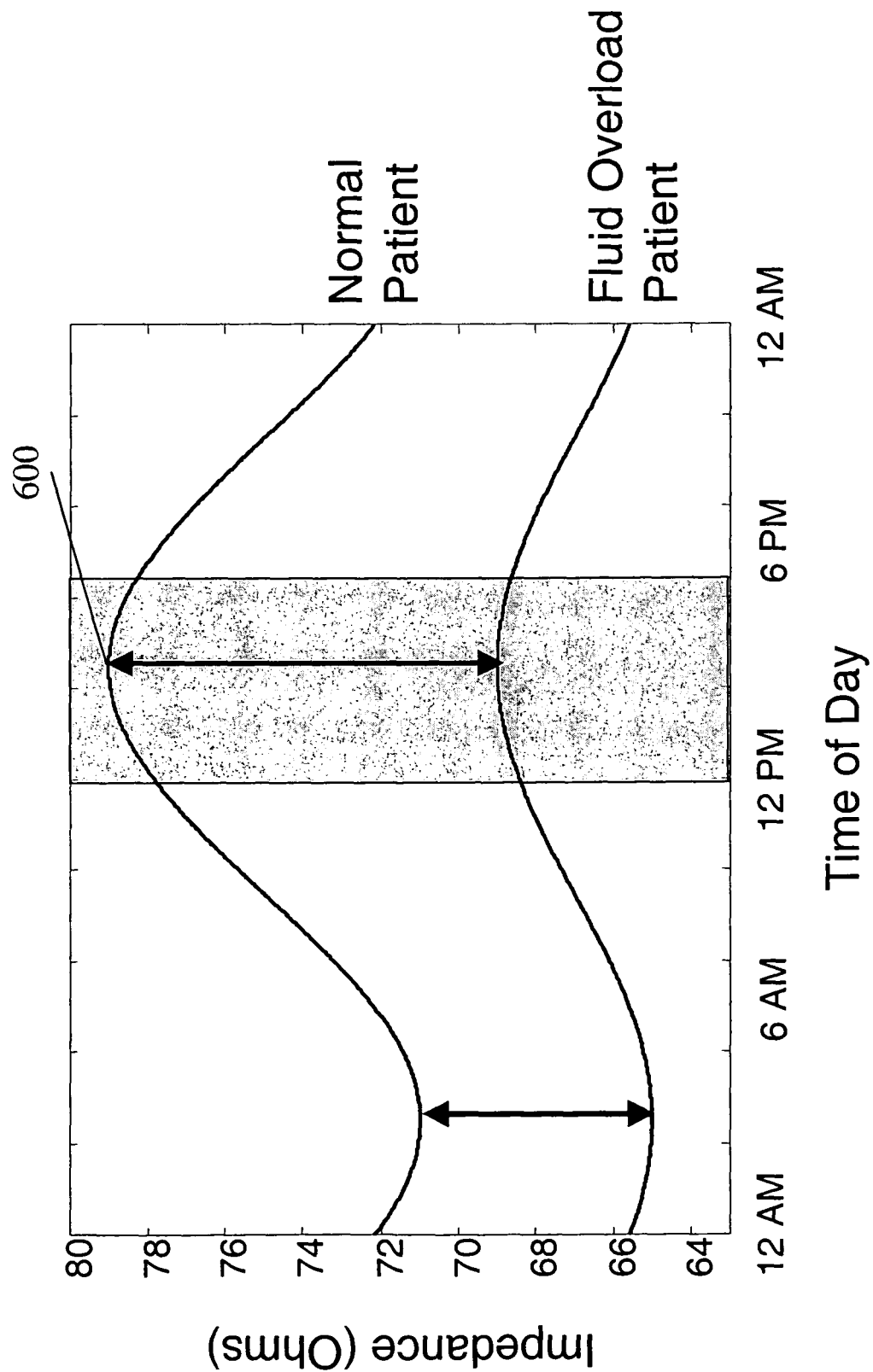
FIG. 10 is a graphical representation of the diurnal variation in impedance versus fluid overload state variation in impedance.

FIG. 10 is a graphical representation of the diurnal variation in impedance versus fluid overload state variation in impedance. The inventors have determined that obtaining the impedance values during the predetermined time period of between 12 pm to 5 pm is advantageous since, as illustrated in FIG. 10, diurnal variation of impedance is greater when the patient is healthy compared to the impedance variation seen when the patient is in a fluid overload state. As a result, the difference between the normal diurnal variation of impedance and the impedance variation seen when the patient is in a fluid overload state is greater at a peak impedance 600 that occurs in the diurnal cycle between 12 pm and 5 pm.

As illustrated in FIG. 9, once the impedance measurement feature is initiated by microprocessor 224, microprocessor 224 initiates parameters for determining changes in impedance according to the present invention by setting the baseline impedance BL, the short term average impedance STA, and the integral of the difference (IntDiff) between the baseline impedance BL and the calculated period average impedance 400 equal to zero, and setting an impedance measurement counter equal to a preset predetermined number of measurements, Step 500. The predetermined number of measurements is chosen according to the number of days that are desired for initiating the baseline impedance BL and the short term average impedance STA parameters. For example, in an embodiment in which the period average impedance 400 is calculated four times per day, graphically represented in FIG. 8, and it is desired that the baseline impedance BL and the short term average impedance STA parameters be initialized within three days, the predetermined number of measurements would be equal to 12 measurements (4 measurements/day for 3 days=12 measurements) and therefore the impedance measurement counter would be initialized by being set equal to 12 in Step 500. On the other hand, in an embodiment in which the period average impedance 400 is calculated once per day, graphically represented in FIG. 8A, and it is desired that the baseline impedance BL and the short term average impedance STA parameters be initialized within four days, the predetermined number of measurements would be equal to 4 measurements (1 measurement/day for 4 days=4 measurements) and therefore the impedance measurement counter would be initialized by being set equal to 4 in Step 500.

Once the parameters have been initialized in Step 500, initial values of the baseline BL impedance and the short term average STA impedance are determined, Step 502, based on the calculated period average impedance generated a predetermined number of times over a period of days associated with the impedance measurement counter.

Figure 11:
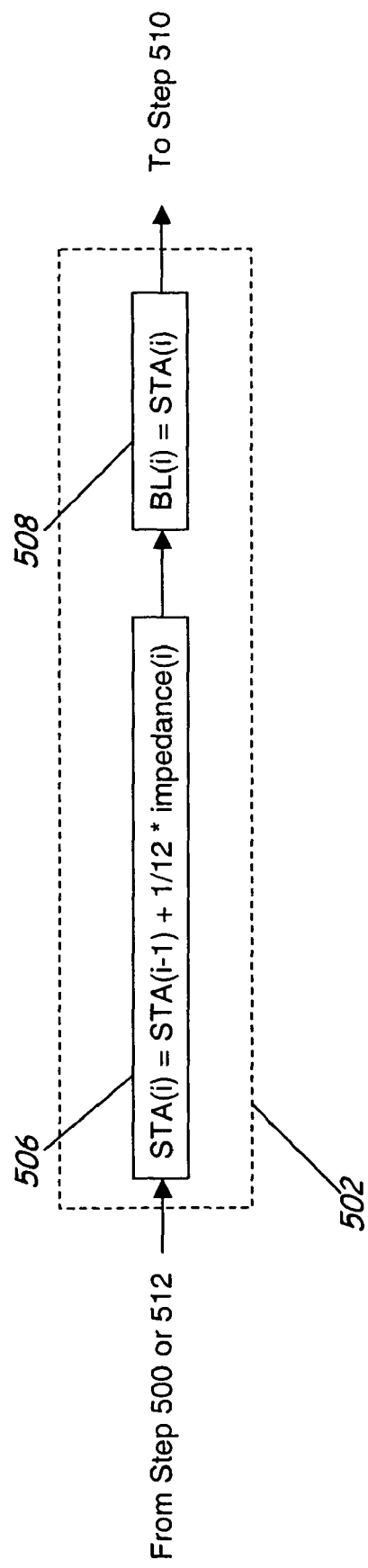
FIG. 11 is an exemplary schematic diagram illustrating obtaining initial baseline impedance and short term average impedance values, according to an embodiment of the present invention.

FIG. 11 is an exemplary schematic diagram illustrating obtaining initial baseline impedance and short term average impedance values, according to an embodiment of the present invention. In particular, as illustrated in FIGS. 9 and 11, in an embodiment of the present invention, the initial values for the baseline BL impedance and the short term average STA impedance are determined, for example, by calculating an average of period average impedance measurements calculated over a predetermined number of days and over a predetermined period of time during each day, as described above. As a result, a short term average impedance STA(i) is equal to the sum of the previously calculated short-term average impedance STA(i−1) and the current calculated period average impedance, impedance(i), divided by the predetermined number of measurements associated with the measurement counter, i.e., 12 measurements for example, Step 506. Once the short term average impedance STA(i) is determined, the baseline impedance BL(i) is updated by being set equal to the short term average impedance STA(i), Step 508, and the impedance measurement counter is decremented, Step 510. Once a next valid period average impedance is received, Step 511, a determination is made as to whether all period average impedance measurements have been made by determining whether the impedance measurement counter is greater than zero, Step 512.

If all period average impedance measurements have not been made and therefore the impedance measurement counter is determined to be greater than zero, YES in Step 512, the averaging process is repeated, Steps 520-512. It is understood that the present invention is not intended to be limited to the averaging scheme illustrated in Steps 502-512, and therefore the present invention is not intended to be limit to determining an average of the period average impedances using the averaging scheme illustrated in FIG. 11. Rather the average of the period average impedances may be calculated using any other known averaging scheme or schemes.

Once all period average impedance measurements have been made and therefore the initial values of the baseline BL impedance and the short term average STA impedance are determined, NO in Step 512, the short term average impedance STA and the baseline impedance BL are updated, Steps 514 and 516.

Figure 12:
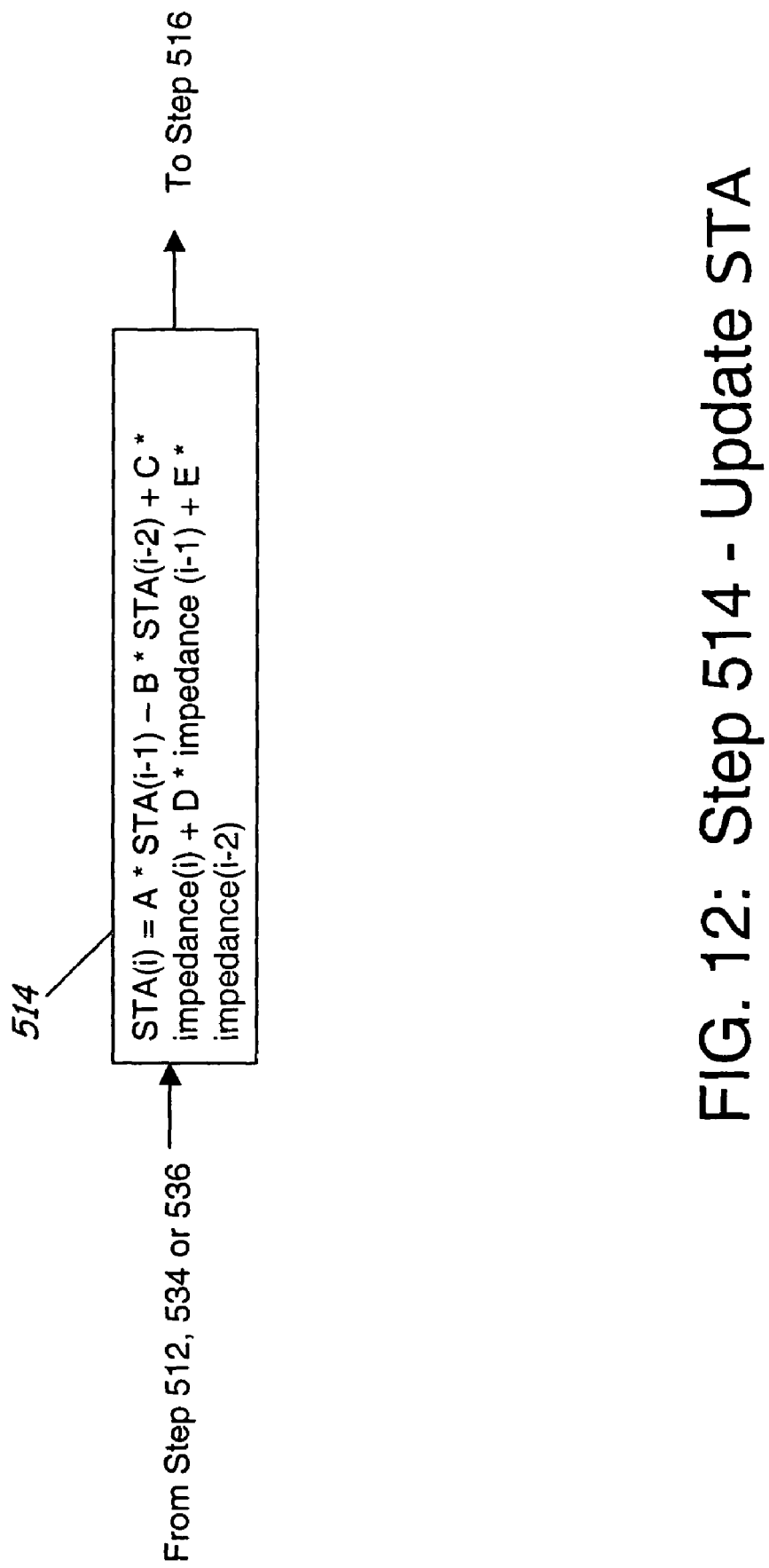
FIG. 12 is an exemplary schematic diagram illustrating updating of short term average impedance values, according to an embodiment of the present invention.

FIG. 12 is an exemplary schematic diagram illustrating updating of short term average impedance values, according to an embodiment of the present invention. As illustrated in FIG. 12, according to an embodiment of the present invention, the short term average impedance STA(i) is updated according to a second order low pass filter. In particular, the short term average STA(i) impedance is updated by taking a weighted sum of the short term average for the two previous days, A*STA(i−1) and B*STA(i−2), respectively, and the period average impedance calculated for the current day, C*impedance (i), and the two previous days, D*impedance (i−1) and E*impedance (i−2), respectively.

By way of example, according to an embodiment of the present invention in which the period average impedance 400 are calculated once per day, using 512 raw impedance measurements collected between 12 pm and 5 pm, illustrated in FIG. 8A, and impedance measurement counter is initialized at 4 measurements, weighted variable A is equal to 77/256, weighted variable B is equal to 50/256, weighted variable C is equal to 60/256, weighted variable D is equal to 109/256 and weighted variable E is equal to 60/256. On the other hand, according to an embodiment of the present invention in which the period average impedance 400 are calculated four times per day, using 512 raw impedance measurements collected between the hours of 12-6 am, 6 am-12 pm, 12 pm-6 pm, and 6 pm-12 am, illustrated in FIG. 8, and impedance measurement counter is initialized at 12 measurements, weighted variable A is equal to 75/64, weighted variable B is equal to 27/64, weighted variable C is equal to 8/64, weighted variable D is equal to zero and weighted variable E is equal to 8/64. However, it is understood that according to the present invention, weighted variables A-E are not intended to be limited to these values, and the low pass filter is not intended to be limited to a second order low pass filter.

Figure 13:
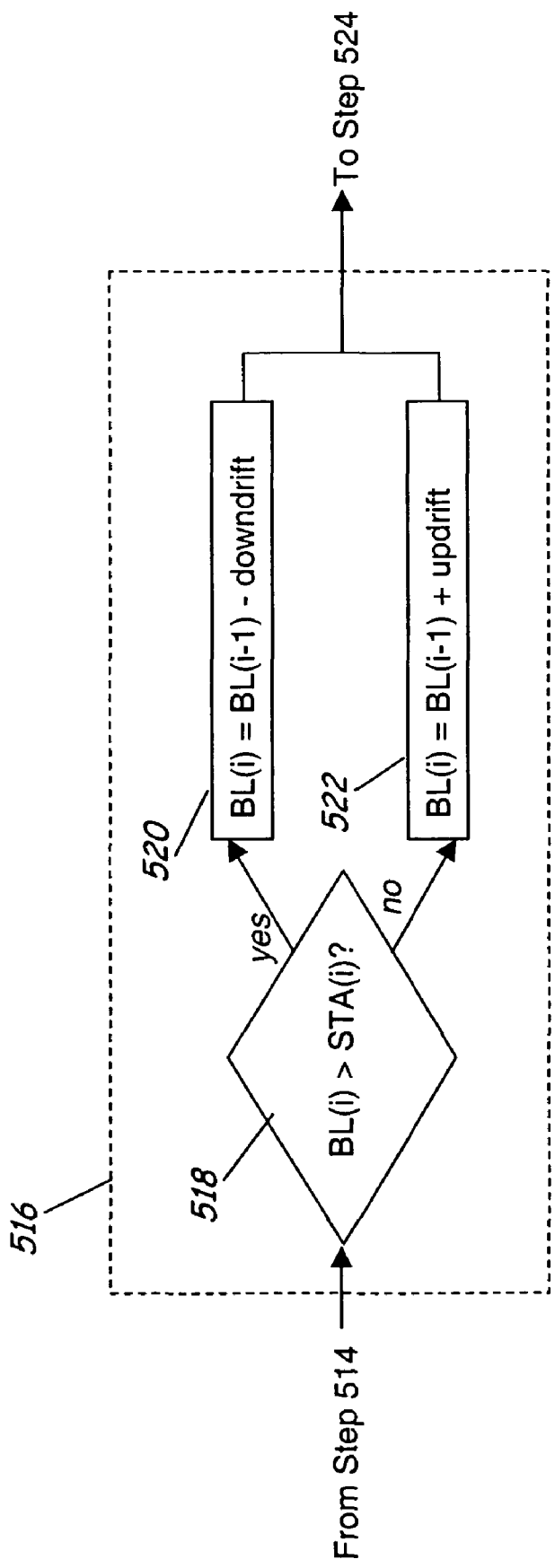
FIG. 13 is an exemplary schematic diagram illustrating updating of baseline impedance values, according to an embodiment of the present invention.

According to the present invention, the baseline impedance is updated at a much slower rate than the short term average impedance. FIG. 13 is an exemplary schematic diagram illustrating updating of baseline impedance values, according to an embodiment of the present invention. As illustrated in FIGS. 9 and 13, according to an embodiment of the present invention, during the updating of the baseline BL impedance 402 in Step 516, once the short term average impedance is updated in Step 514, microprocessor 224 determines the location of the short term average impedance STA(i) relative to the current baseline impedance BL(i) by determining whether the baseline impedance 402 is greater than the short term average impedance STA(i), Step 518. If the current baseline impedance BL(i) is greater than the short term average impedance STA(i), YES in Step 518, the current baseline impedance BL(i) is updated by being set equal to the previous baseline impedance BL(i−1) reduced by a predetermined downdrift, Step 520. On the other hand, if the current baseline impedance BL(i) is not greater than the short term average impedance STA(i), NO in Step 518, the current baseline impedance BL(i) is updated by being set equal to the previous baseline impedance BL(i−1) increased by a predetermined updrift, Step 522.

According to the present invention, in order to make the device 100 more sensitive to decreases in impedances, the downdrift in Step 520 is set so as to be less than the updrift in Step 522. For example, according to an embodiment of the present invention, the downdrift is set to be approximately equal to 0.055 ohms per day and the updrift is set to be approximately equal to 0.18 ohms per day, although other values may be utilized as desired. The method of updating the value of the baseline BL impedance could also be based upon lowpass filters with either the current impedance or the short term average STA impedance as the input. The inventors have determined that a faster rate of growth than decline of BL is highly advantageous for predicting hospitalizations for fluid overload while avoiding false alarms.

Returning to FIG. 9, once the short term average impedance 404 and baseline impedance 402 have been updated, microprocessor 224 determines whether the relative position of the short term average impedance and the baseline impedance has changed, such as would occur if either the short term average impedance 404 was less than the baseline impedance 402 but is now greater than or equal to baseline impedance 402, or the short term average impedance 404 was greater than the baseline impedance 402 but is now less than or equal to baseline impedance 402, Step 524. In particular, as illustrated in FIG. 8A for example, since a calculated short term average impedance 403 corresponding to the previous day is less than the baseline impedance 402, and a calculated short term impedance 405 corresponding to the current day is greater than the baseline impedance 402, the short term average impedance 404 crosses the baseline impedance 402, YES in Step 524. On the other hand, since a calculated short term average impedance 407 corresponding to the previous day is greater than the baseline impedance 402, and a calculated short term impedance 409 corresponding to the current day is less than the baseline impedance 402, the short term average impedance 404 crosses the baseline impedance 402, YES in Step 524. Such crossing of the baseline impedance 402 by the short term average impedance 404 is an indication that there is no longer any evidence to suspect the existence of an abnormal impedance, indicative of fluid accumulation or dehydration.

As illustrated in FIG. 9, if it is determined that short term average impedance 404 crosses baseline impedance 402, YES in Step 524, microprocessor 224 sets the integral of the difference between the period average impedance and the baseline impedance (IntDiff) 412 equal to zero, Step 526. On the other hand, if it is determined that short term average impedance 404 does not cross baseline impedance 402, NO in Step 524, microprocessor 224 updates the integral of the difference between the period average impedance and the baseline impedance (IntDiff) 412 by adding the current difference between the current calculated period average impedance 400 and the baseline impedance 402, Step 528. A determination is then made as to whether significant changes in impedance have occurred, Step 530.

According to an embodiment of the present invention, the determination in Step 530 as to whether a significant change in impedance has occurred is made, for example, by determining whether the updated integral of the difference between the period average impedance and the baseline impedance (IntDiff) 412 is less than a predetermined IntDiff threshold 416. According to another embodiment of the present invention, the determination in Step 530 as to whether a significant change in impedance has occurred can be made by determining whether the difference between the short term average impedance and the baseline impedance STA-BL is less than a predetermined threshold 418, by determining whether the baseline impedance is less than a predetermined baseline impedance threshold 420, or by determining whether any combination of IntDiff 412, STA-BL and the baseline impedance is less than the respective thresholds 416420.

The parameter corresponding to the difference between the short term average impedance and the baseline impedance STA-BL is similar to that described in U.S. Pat. No. 5,957,861 to Combs et al., incorporated herein by reference in its entirety, and is a less useful indicator of the presence of significant change in impedance, when the measured impedance declines slowly for weeks before hospital admission. However, the STA-BL parameter may be useful in those patients with very rapid decompensation of heart failure. Finally, the direct thresholding of the BL parameter is the simplest programmed threshold and may have value for detecting extremely slow disease processes.

If it is determined that a significant change in impedance has occurred, YES in Step 530, an alarm or patient indicator is activated, via patient notification circuit 331, to inform the patient of the condition, Step 532. For example, an alarm is activated when the difference between the calculated short term average impedance and the calculated baseline impedance as a percentage of the baseline impedance 408 generated in plot 410 of FIGS. 8 and 8A is less than threshold 418, or when IntDiff 412 generated in plot 414 is less than threshold 416, or when the baseline BL impedance is less than a predetermined baseline impedance threshold. It is understood that while thresholds 416 and 418 are illustrated as being equal to –60 Ohms and –10 Ohms, respectively, the present invention is not intended to be limited to those values. Rather, according to the present invention, thresholds 416 and 418 can be programmed by the clinician as any desired value. In the same way, baseline impedance threshold 420 is patient specific and therefore may be preprogrammed by the clinician to any value deemed appropriate for a specific patient.

According to the present invention, the alarm of Step 532 could include an audible alarm, vibration, stimulation, communication to an external device via telemetry circuitry 330 for transmission to an external database or communication network, for example. According to an embodiment of the present invention, in addition to merely alerting the patient and/or an outside entity of the detection of fluid accumulation or dehydration based on changes in impedance, a therapy may also be initiated or modified, Step 533, in response to the detection of fluid accumulation or dehydration based on changes in impedance. Such therapies could include, for example, a drug pump, a pacing mode, a pacing rate, cardiac resynchronization therapy (CRT), cardiac potentiation therapy (CPT), etc. In addition, according to an embodiment of the present invention, the algorithm for detecting changes in impedance could also be modified, Step 533, in response to the detection of fluid accumulation or dehydration based on changes in impedance. For example, the number of times that the period average impedance 400 is generated could be increased to a faster rate from the initial rate, i.e., from once per day to once an hour.

Whether or not therapy is initiated or modified or the algorithm for detecting changes in impedance is modified in response to determining changes in impedance is programmable and therefore optional. As a result, once the alarm has been activated, Step 532, a determination is made as to whether a therapy or the algorithm for detecting changes in impedance should be modified or initiated, Step 533. If so, the therapy and/or the algorithm for detecting changes in impedance is initiated or modified, Step 535. Once either the alarm has been activated in Step 532 and no therapy/algorithm modification/initiation is set, NO in Step 33, or the alarm has been activated and a therapy/algorithm has been modified or initiated, YES in Step 533 and Step 535, or once it is determined that a significant change in impedance has not occurred, NO in Step 530, the process waits for the next valid period average impedance 400 of individual raw impedance measurements collected a predetermined number of times per day during a predetermined time period to be generated, Step 534, and the process of Steps 514-532 is repeated.

Once the IntDiff 412 parameter has exceeded the predetermined threshold and an alert has been issued, the alert will continue to activate each day until IntDiff 412 parameter is cleared, Step 526. Clearing of IntDiff 412 parameter occurs when the short term average STA crosses over the baseline BL impedance, indicating that there is no longer evidence of abnormal impedance. Cessation of the alarm condition as stated above is advantageous to the clinician and patient, because it can be used to indicate that the corrective action that was taken upon initiation of the alert condition (e.g., increased dose of a diuretic) was successful in correcting the condition.

According to an embodiment of the present invention, once the next valid period average impedance 400 of individual raw impedance measurements collected a predetermined number of times per day during a predetermined time period is generated, Step 534, a determination is made as to whether a command has been received via telemetry circuit 330 to reset the algorithm, Step 536. This feature is optional and is convenient for establishing new initial values of BL and STA after an intervention that rapidly changes the measured impedance (such as administration of intravenous diuretics). The user can command the algorithm to reset immediately, or to reset after a programmable delay (e.g., 1 week). The delay is useful to force a reset only after the patient's status is predicted to stabilize, such as after ingestion of medication by the patient, for example. The command to reset the algorithm can be received using the activation describe, for example, in commonly assigned U.S. Pat. No. 5,836,975 to DeGroot et al., incorporated herein by reference in its entirety.

Figure 14:
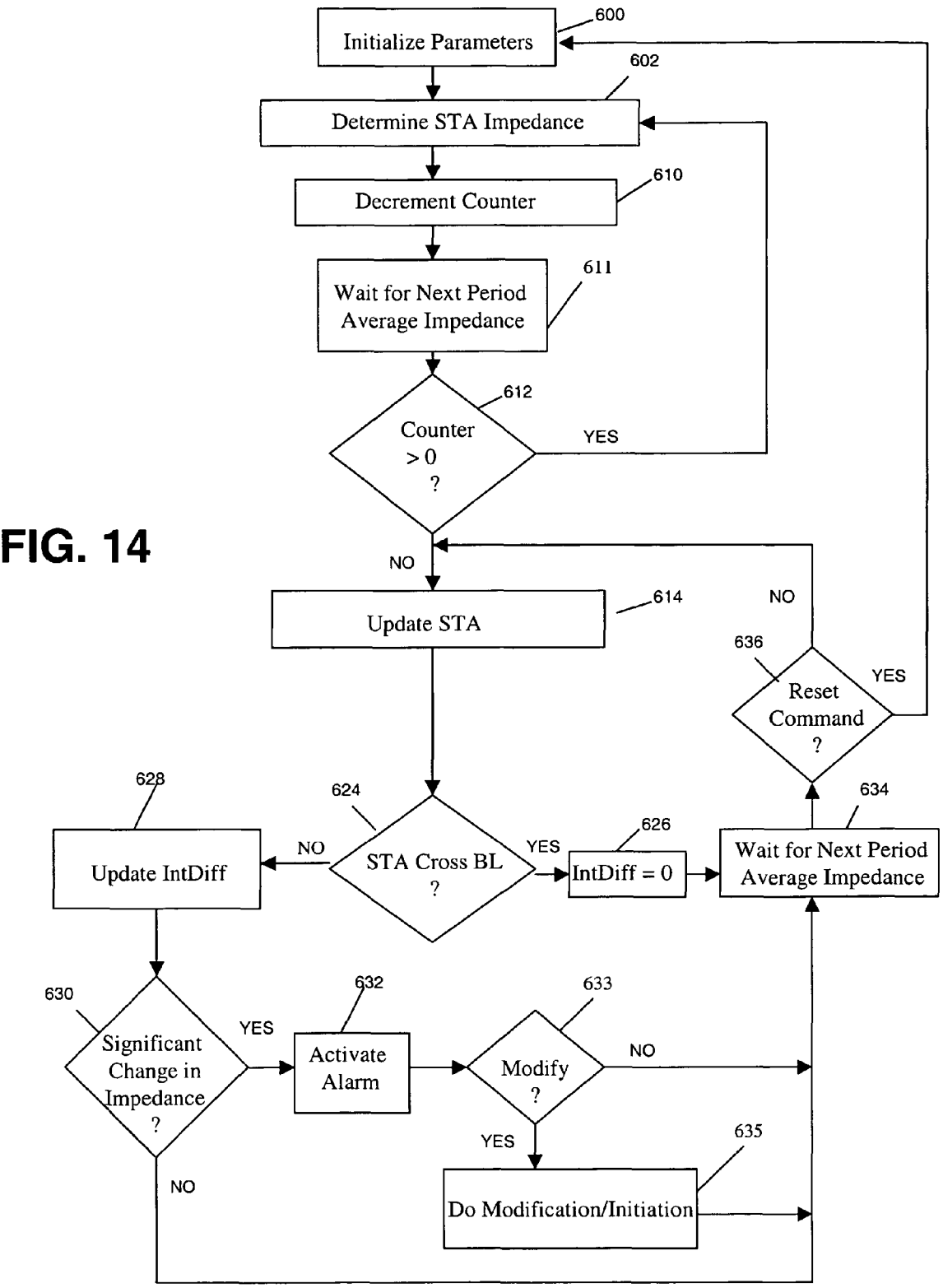
FIG. 14 is a flowchart of a method illustrating a method for determining changes in impedance according to an embodiment of the present invention.

FIG. 14 is a flowchart of a method illustrating a method for determining changes in impedance according to an embodiment of the present invention. The method for determining changes in impedance illustrated in FIG. 14 is similar to the method described above in reference to FIG. 9, however, during initialization of Step 600 in the embodiment of FIG. 14, the baseline impedance is set equal to a predetermined value, Step 608, input by the physician during implant of the device. The baseline impedance then maintains this predetermined value throughout the process of determining changes in impedance, rather than being updated automatically in response to the calculated period average impedance. As a result, the step of updating the baseline impedance, Step 516, in the embodiment of FIG. 9 is not included in the embodiment of FIG. 14.

FIG. 15 is an exemplary schematic diagram illustrating obtaining initial short term average impedance values, according to an embodiment of the present invention. As illustrated in FIG. 15, since the baseline impedance maintains the predetermined value obtained during initializtion, Step 600, the embodiment of FIG. 14 differs from the embodiment of FIG. 9 in that once the parameters are initialized, Step 600, an initial value is determined only for the short term average impedance, Step 606, and not for the baseline impedance.

In addition, in the embodiment of FIG. 14, the determination of whether a significant change in impedance has occurred is made in Step 630 by determining whether the updated integral of the difference between the period average impedance and the baseline impedance (IntDiff) 412 is less than predetermined IntDiff threshold 416. According to another embodiment of the present invention, the determination in Step 630 as to whether a significant change in impedance has occurred can be made by determining whether the difference between the short term average impedance and the baseline impedance STA-BL is less than a predetermined threshold 418, and in yet another embodiment by determining whether any combination of IntDiff 412 and STA-BL is less than the respective thresholds 416 and 418. The remainder of the steps involved in the embodiment of FIG. 14 are similar to the corresponding steps described above in reference to the embodiment of FIG. 9, and therefore are not repeated merely for the sake of brevity.

By maintaining the selected predetermined value for the baseline impedance through the process, the embodiment of FIG. 14 enables a clinician who is familiar with the specific physiologic tendencies of a patient and who desires to have the ability to set the baseline impedance for that patient at a specific predetermined value, say 75 Ohms, for example, so that the baseline impedance maintains that predetermined value throughout the process of determining change in impedance according to the present invention.

Measurement of intrathoracic impedance according to the present invention can be utilized, as described above, for detecting onset of pulmonary congestion/edema, as well for detection of dehydration of the patient (signaled by an increase in the impedance) or the presence of worsening of other disease processes like pulmonary fibrosis, asthma, or COPD.

Some of the techniques described above may be embodied as a computer-readable medium comprising instructions for a programmable processor such as microprocessor 224 or pacer timing/control circuitry 212 shown in FIG. 7. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

While a particular embodiment of the present invention has been shown and described, modifications may be made. It is therefore intended in the appended claims to cover all such changes and modifications, which fall within the true spirit and scope of the invention.

What is claimed is:

1. An implantable medical device for detection of changes in impedance in a patient, comprising:

means for generating measured impedances;

means for generating an adaptive baseline trend of the measured impedances corresponding to a first time;

means for generating a short term trend of the measured impedances corresponding to a second time period less than the first time;

means for accumulating a difference between the adaptive baseline trend and one of a most recent measured impedance and the short term trend of the measured impedances; and means for updating the adaptive baseline trend by setting the adaptive baseline trend equal to a previous adaptive baseline trend reduced by a predetermined downdrift in response to the current adaptive baseline trend being greater than the current short term trend, and by setting the adaptive baseline trend equal to the previous adaptive baseline trend increased by a predetermined updrift in response to the current adaptive baseline trend being less than the current short term trend, wherein the updrift is greater than the downdrift.

2. The implantable medical device of claim 1, wherein the downdrift is approximately equal to 0.055 ohms and the updrift is approximately equal to 0.18 ohms.

3. The implantable medical device of claim 1, wherein the means for accumulating a difference sets the accumulated difference equal to zero in response to the short term trend being equal to the adaptive baseline trend.

4. A method for detection of changes in impedance a patient, comprising:

generating measured impedances;

generating an adaptive baseline trend of the measured impedances corresponding to a first time period;

generating a short term trend of the measured impedances corresponding to a second time period less than the first time period; and generating an accumulated difference between the adaptive baseline trend and one of a most recent measured impedance and the short term trend of the measured impedances; and updating the adaptive baseline trend by setting the adaptive baseline trend equal to a previous adaptive baseline trend reduced by a predetermined downdrift in response to the current adaptive baseline trend being greater than the current short term trend, and by setting the adaptive baseline trend equal to the previous adaptive baseline trend increased by a predetermined updrift in response to the current adaptive baseline trend being less than the current short term trend, wherein the updrift is greater than the downdrift.

5. The method of claim 4, wherein the downdrift is approximately equal to 0.055 ohms and the updrift is approximately equal to 0.18 ohms.

* * * * *